(12) United States Patent
Perkins et al.

(10) Patent No.: US 10,496,776 B2
(45) Date of Patent: Dec. 3, 2019

(54) FABRICATION OF CRITICAL LAYERS OF INTEGRATED COMPUTATIONAL ELEMENTS

(71) Applicant: Halliburton Energy Services, Inc., Houston, TX (US)

(72) Inventors: David L. Perkins, The Woodlands, TX (US); Robert Paul Freese, Pittsboro, NC (US); Christopher Michael Jones, Houston, TX (US); Richard Neal Gardner, Raleigh, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 1087 days.

(21) Appl. No.: 14/390,841

(22) PCT Filed: Dec. 24, 2013

(86) PCT No.: PCT/US2013/077685
§ 371 (c)(1),
(2) Date: Oct. 6, 2014

(87) PCT Pub. No.: WO2015/099707
PCT Pub. Date: Jul. 2, 2015

(65) Prior Publication Data
US 2016/0292338 A1    Oct. 6, 2016

(51) Int. Cl.
*G06F 17/50* (2006.01)
*C23C 14/54* (2006.01)
(Continued)

(52) U.S. Cl.
CPC ........ *G06F 17/5068* (2013.01); *C23C 14/546* (2013.01); *C23C 14/547* (2013.01);
(Continued)

(58) Field of Classification Search
CPC ... C23C 14/547; C23C 14/541; C23C 14/545; C23C 14/50; G01N 21/31; G01N 21/833;
(Continued)

(56) References Cited

U.S. PATENT DOCUMENTS

| 5,075,550 A | 12/1991 | Miller et al. |
| 5,399,229 A | 3/1995 | Stefani et al. |

(Continued)

FOREIGN PATENT DOCUMENTS

| WO | WO 2004/015364 | 2/2004 |
| WO | WO 2005045891 A2 * | 5/2005 ........... C23C 14/546 |

(Continued)

OTHER PUBLICATIONS

International Search Report and Written Opinion of the International Searching Authority issued in International Application No. PCT/US2013/077685 dated Sep. 1, 2014; 8 pages.

(Continued)

*Primary Examiner* — Michael P Wieczorek
*Assistant Examiner* — Michael G Miller
(74) *Attorney, Agent, or Firm* — Benjamin Fite; Parker Justiss, P.C.

(57) ABSTRACT

A design of an integrated computational element (ICE) includes (1) specification of a substrate and multiple layers, their respective target thicknesses and refractive indices, refractive indices of adjacent layers being different from each other, and a notional ICE fabricated based on the ICE design being related to a characteristic of a sample, and (2) identification of one or more critical layers of the ICE layers, an ICE layer being identified as a critical layer if potential variations of its thickness or refractive index due to expected fabrication variations cause ICE performance degradation that exceeds a threshold degradation, otherwise the ICE layer being identified as a non-critical layer. At least one (Continued)

critical layer of the ICE is formed using two or more forming steps to form respective two or more sub-layers of the critical layer, and at least one non-critical layer of the ICE is formed using a single forming step.

23 Claims, 11 Drawing Sheets

(51) Int. Cl.
    *G01N 21/21*     (2006.01)
    *G01N 21/27*     (2006.01)
    *G02B 5/28*     (2006.01)
    *C23C 14/10*     (2006.01)
    *C23C 14/16*     (2006.01)
    *C23C 14/18*     (2006.01)

(52) U.S. Cl.
    CPC .......... *G01N 21/211* (2013.01); *G01N 21/27* (2013.01); *G02B 5/285* (2013.01); *C23C 14/10* (2013.01); *C23C 14/16* (2013.01); *C23C 14/18* (2013.01)

(58) Field of Classification Search
    CPC ............... G01N 21/8422; G01N 21/84; G01N 33/2823; G01N 2021/8411; G01N 2021/8438; E21B 49/08
    USPC .................................................. 427/160–169
    See application file for complete search history.

(56) References Cited

U.S. PATENT DOCUMENTS

| | | | |
|---|---|---|---|
| 5,453,716 A | 9/1995 | Person et al. | |
| 5,537,479 A | 7/1996 | Kreisel et al. | |
| 5,619,366 A | 4/1997 | Rhoads et al. | |
| 6,078,389 A | 6/2000 | Zetter | |
| 6,154,550 A | 11/2000 | Beyer | |
| 6,163,259 A | 12/2000 | Barsumian et al. | |
| 6,198,531 B1 | 3/2001 | Myrick et al. | |
| 6,213,250 B1 | 4/2001 | Wisniewski et al. | |
| 6,217,720 B1 * | 4/2001 | Sullivan ................ | C23C 14/548 204/192.13 |
| 6,529,276 B1 | 3/2003 | Myrick | |
| 6,646,753 B2 | 11/2003 | Zhang et al. | |
| 6,804,060 B1 | 10/2004 | Tsai et al. | |
| 6,905,578 B1 | 6/2005 | Moslehi et al. | |
| 6,965,431 B2 | 11/2005 | Vo-Dinh et al. | |
| 7,138,156 B1 * | 11/2006 | Myrick .................. | G02B 5/285 359/359 |
| 7,163,901 B2 | 1/2007 | Downey | |
| 7,332,044 B2 | 2/2008 | Sidorin et al. | |
| 7,679,563 B2 | 3/2010 | Werner et al. | |
| 7,697,141 B2 | 4/2010 | Jones et al. | |
| 7,753,847 B2 | 7/2010 | Greenleaf et al. | |
| 7,777,870 B2 | 8/2010 | Hayes et al. | |
| 7,792,644 B2 | 9/2010 | Kotter et al. | |
| 7,828,929 B2 | 11/2010 | Lee et al. | |
| 7,911,605 B2 | 3/2011 | Myrick et al. | |
| 7,920,258 B2 | 4/2011 | Myrick et al. | |
| 8,054,212 B1 | 11/2011 | Holly et al. | |
| 8,106,850 B1 | 1/2012 | Gregoire et al. | |
| 8,164,061 B2 | 4/2012 | Pawlak et al. | |
| 8,216,161 B2 | 7/2012 | Darlington et al. | |
| 8,252,112 B2 | 8/2012 | Ovshinsky | |
| 8,300,313 B2 * | 10/2012 | Pradhan .................... | G01J 3/10 359/359 |
| 2005/0054928 A1 | 3/2005 | Cerofolini | |
| 2006/0055935 A1 | 3/2006 | Cheben et al. | |
| 2007/0100580 A1 | 5/2007 | Marcus et al. | |
| 2008/0237492 A1 | 10/2008 | Caliendo et al. | |
| 2009/0182693 A1 | 7/2009 | Fulton et al. | |
| 2012/0268744 A1 | 10/2012 | Wolf et al. | |
| 2013/0284894 A1 | 10/2013 | Freese et al. | |
| 2013/0284895 A1 | 10/2013 | Freese et al. | |
| 2013/0284896 A1 | 10/2013 | Freese et al. | |
| 2013/0284897 A1 | 10/2013 | Freese et al. | |
| 2013/0284898 A1 | 10/2013 | Freese et al. | |
| 2013/0284899 A1 | 10/2013 | Freese et al. | |
| 2013/0284900 A1 | 10/2013 | Freese et al. | |
| 2013/0284901 A1 | 10/2013 | Freese et al. | |
| 2013/0284904 A1 | 10/2013 | Freese et al. | |
| 2013/0286398 A1 | 10/2013 | Freese et al. | |
| 2013/0286399 A1 | 10/2013 | Freese et al. | |
| 2013/0287061 A1 | 10/2013 | Freese et al. | |

FOREIGN PATENT DOCUMENTS

| | | |
|---|---|---|
| WO | WO 2006/031733 | 3/2006 |
| WO | WO 2007/015115 | 2/2007 |
| WO | WO 2008/106391 | 9/2008 |
| WO | WO 2011/103066 | 8/2011 |
| WO | WO2012108885 | 8/2012 |
| WO | WO 2013/022556 | 2/2013 |
| WO | WO2015099671 | 7/2015 |

OTHER PUBLICATIONS

International Search Report and Written Opinion of the International Searching Authority issued in International Application No. PCT/US2013/077683 dated Sep. 1, 2014; 9 pages.
Frey et al., "Temperature-dependent refractive index of silicon and germanium," NASA Goodard Space Flight Center, Greenbelt, MD, 2006, 10 pages.
Morton et al., "Optical Monitoring of Thin-films Using Spectroscopic Ellipsometry," Society of Vacuum Coaters, 45th Annual Technical Conference Proceedings, 2002, 7 pages.
Eastwood et al., "Field applications of stand-off sensing using visible/NIR multivariate optical computing," Department of Chemistry and Biochemistry, University of South Carolina, SPE vol. 4199, 2001, 10 pages.
Paul et al., "Fabrication of mid-infrared frequency-selective surfaces by soft lithography", Applied Optics, v. 40, No. 25, Sep. 2001, 5 pages.
Haibach et al., "Precision in multivariate optical computing," Applied Optics, vol. 43, No. 10, Apr. 1, 2004, 11 pages.
J.A. Woollam Co., Inc., Characterizing Processes with EASE® In Situ Applications, Application Note, 2009, 3 pages.
Li, "Refractive Index of Silicon and Germanium and Its Wavelength and Temperature Derivatives," Center for Information and Numerical Data Analysis and Synthesis, Purdue University, J. Phys. Chem. Ref. Data, vol. 9, No. 3, 1980, 98 pages.
Myrick, "Multivariate optical elements simplify spectroscopy," Laser Focus World, Mar. 1, 2002, access date Feb. 28, 2013, 3 pages http://www.laserfocusworld.com/articles/print/volume-38/issue-3/features/spectroscopy/multivariate-optical-elements-simplify-spectroscopy.html.
Myrick et al., "A single-element all-optical approach to chemometric prediction," Vibrational Spectroscopy 28, 2002, 9 pages.
Myrick et al., "Spectral tolerance determination for multivariate optical element design," Fresenius J Anal Chem, 369, 2001, 5 pages.
Myrick et al., "Application of multivariate optical computing to simple near-infrared point measurements," SPIE vol. 4574, Department of Chemistry and biochemistry, University of South Carolina, 2002, 8 pages.
Rabady et al., "High-resolution photometric optical monitoring for thin-film deposition," Applied Optics, Optical Society of America, vol. 43, No. 1, Jan. 1, 2004, 6 pages.
Priore et al., "Novel Imaging Systems: Multivariate Optical Computing in the UV-VIS," Department of Chemistry and Biochemistry, University of South Carolina, 2003, 5 pages.
Grader et al., "Fourier transform infrared spectroscopy of a single aerosol particle," J. Chem. Phys. 86 (11), Jun. 1, 1987, 7 pages.
Soyemi et al., "Novel Filter Design Algorithm for Multivariate Optical Computing," Advanced Environmental and Chemical Sensing Technology, SPIE vol. 4205, 2001, 12 pages.

(56) References Cited

OTHER PUBLICATIONS

Telemark, "Model 820 In-Situ Spectroscopic Optical Monitor," Dec. 2010, 4 pages.
Bossard et al., "The Design and fabrication of planar multiband metallodielectric frequency selective surfaces for infrared applications", IEEE Trans. on Antennas and Propagation, v. 50, No. 4, Apr. 2006, 12 pages.
Woollam et al., "Overview of Variable Angle Spectroscopic Ellipsometer (VASE), Part 1: Basic Theory and Typical Applications," Society of Photo-Optical Instrumentation Engineers, Critical Reviews of Optical Science Technology CR72, 1999, 28 pages.
Zoeller et al., "Substantial progress in optical monitoring by intermittent measurement technique," SPIE, Published in the processing of the OSD, Jena 2005, vol. 5963-13, 9 pages.
Haibach et al., "On-line Reoptimization of Filter Designs for Multivariate Optical Elements," vol. 42, No. 10, Apr. 1, 2003.
Extended European Search Report, EP 13883845.3, dated Dec. 2, 2015, 7 pages.
Haibach et al., "On-Line Reoptimization of Filter Designs for Multivariate Optical Elements", Optical Society of America, vol. 42, No. 10, Apr. 1, 2003, 6 pages.

* cited by examiner

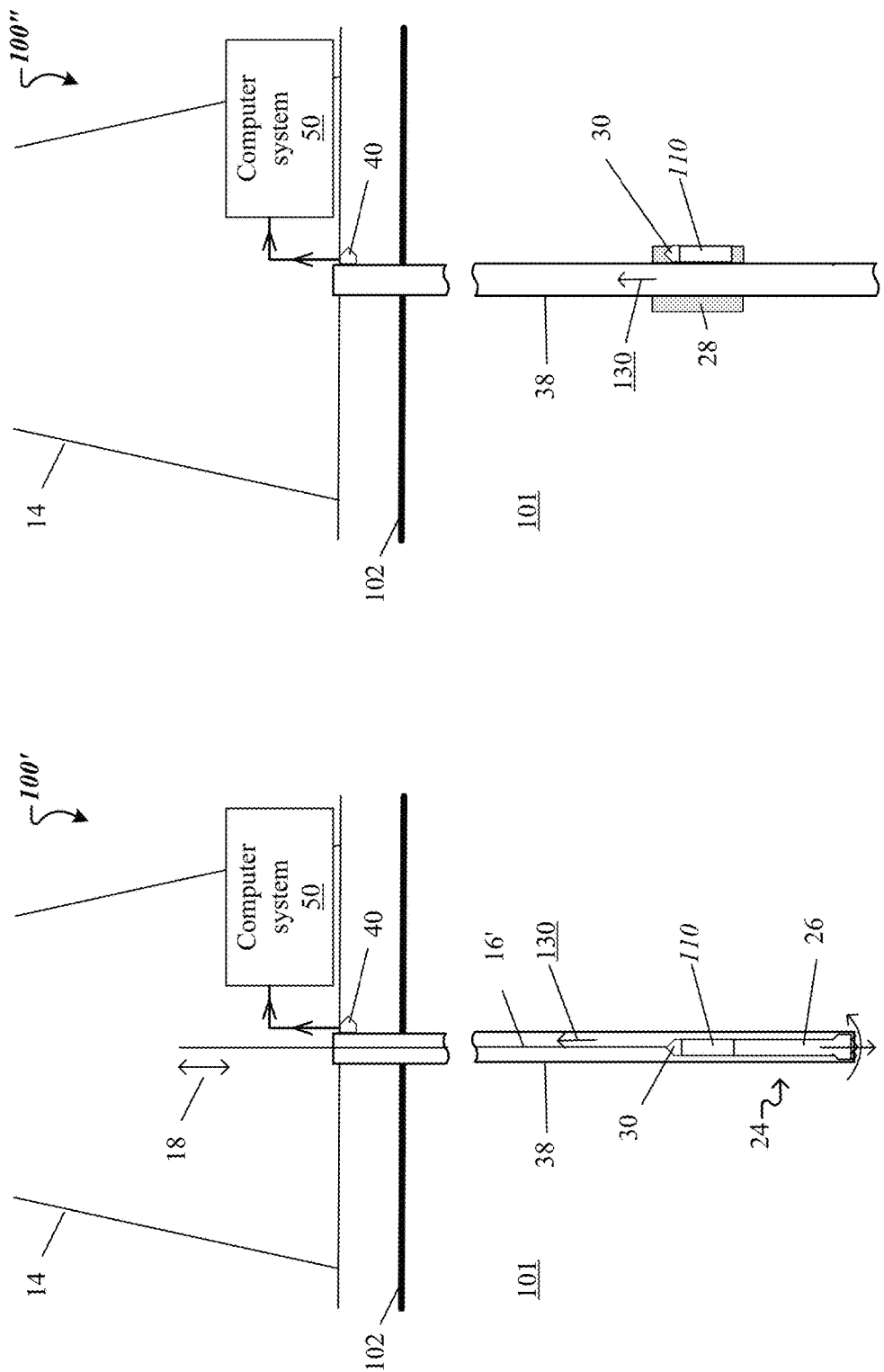

FABRICATION OF CRITICAL LAYERS OF INTEGRATED COMPUTATIONAL ELEMENTS

CLAIM OF PRIORITY

This application is a U.S. National Stage of International Application No. PCT/US2013/077685, filed Dec. 24, 2013.

BACKGROUND

The subject matter of this disclosure is generally related to fabrication of an integrated computational element (ICE) used in optical analysis tools for analyzing a substance of interest, for example, crude petroleum, gas, water, or other wellbore fluids. For instance, the disclosed ICE fabrication relates to forming one or more layers of the ICE that are deemed to be critical.

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

Integrated computational elements (ICEs) enable the measurement of various chemical or physical characteristics through the use of regression techniques. An ICE selectively weights, when operated as part of optical analysis tools, light modified by a sample in at least a portion of a wavelength range such that the weightings are related to one or more characteristics of the sample. An ICE can be an optical substrate with multiple stacked dielectric layers (e.g., from about 2 to about 50 layers), each having a different complex refractive index from its adjacent layers. The specific number of layers, N, the optical properties (e.g. real and imaginary components of complex indices of refraction) of the layers, the optical properties of the substrate, and the physical thickness of each of the layers that compose the ICE are selected so that the light processed by the ICE is related to one or more characteristics of the sample. Because ICEs extract information from the light modified by a sample passively, they can be incorporated in low cost and rugged optical analysis tools. Hence, ICE-based downhole optical analysis tools can provide a relatively low cost, rugged and accurate system for monitoring quality of wellbore fluids, for instance.

Errors in fabrication of some constituent layers of an ICE design can degrade the ICE's target performance. In most cases, deviations of <0.1%, and even 0.01% or 0.0001%, from point by point design values of the optical characteristics (e.g., complex refractive indices), and/or physical characteristics (e.g., thicknesses) of the formed layers of the ICE can reduce the ICE's performance, in some cases to such an extent, that the ICE becomes operationally useless. Those familiar or currently practicing in the art will readily appreciate that the ultra-high accuracies required by ICE designs challenge the state of the art in techniques for adjusting thin film stack fabrication.

Conventionally, prior to or while forming of each of the N layers of the ICE, target thicknesses of one or more layers that remain to be formed are updated based on complex refractive indices and thicknesses of the formed layers. In this manner, degradation in the ICE performance relative to the target performance, caused by potential inaccuracies in the complex refractive indices and thicknesses of the formed layers, can be minimized while forming the remaining ones of the N layers. Moreover, each layer of the N layers of the ICE is conventionally formed as a sequence of successively thinner sub-layers, e.g., 90%, 5%, 2.5%, 1.25% of the total thickness of the layer. In this manner, formation of the layer is completed when a next sub-layer to be formed from the forgoing sequence would not improve the ICE performance relative to the target performance.

DESCRIPTION OF DRAWINGS

FIGS. 1A-1C show multiple configurations of an example of a system for analyzing wellbore fluids that uses a well logging tool including an ICE.

Like reference symbols in the various drawings indicate like elements.

DETAILED DESCRIPTION

Technologies for ICE fabrication disclosed herein can be used to form non-critical layers from among N layers of an ICE such that each non-critical layer is formed using a single forming step, and critical layers from among the N layers of the ICE such that each critical layer is formed using multiple forming steps to form respective sub-layers thereof. A layer of the ICE is identified, e.g., prior to fabrication, as a critical layer if potential variations of its complex refractive index and/or thickness due to expected variations of the fabrication process can cause degradation of the ICE's performance below an acceptable threshold; otherwise the layer is identified as a noncritical layer. A number of the sub-layers to be used in forming each critical layer are determined, at least in part, based on a target thickness of the critical layer and fabrication process/equipment capability.

The disclosed technologies can be used to implement ICE fabrication that can be less complex and less time consuming than conventional ICE fabrication. For instance, a potential advantage of the disclosed technologies is that non-critical layers of the ICE can be formed in one forming step. Hence, duration of the ICE fabrication based on the disclosed technologies can be reduced with respect to the conventional ICE fabrication, where each of the N layers of the ICE is formed as a sequence of sub-layers. Another advantage of the disclosed technologies is that adjusting thicknesses of one or more layers that remain to be formed can be skipped prior to forming of a non-critical layer without compromising the performance of the ICE. Accordingly, both complexity and duration of the ICE fabrication based on the disclosed technologies can be reduced with respect to the conventional ICE fabrication, where thicknesses of the remaining layers are adjusted prior to or while forming of each of the N layers of the ICE.

Prior to describing multiple implementations of the disclosed technologies for ICE fabrication, the following technologies are described below: in Section (1)—optical analysis tools based on ICE along with examples of their use in oil/gas exploration, in Section (2)—techniques for designing an ICE, and in Section (3)—techniques for determining the critical layers of an ICE design.

(1) ICE-Based Analysis of Wellbore Fluids

Figure 1A:
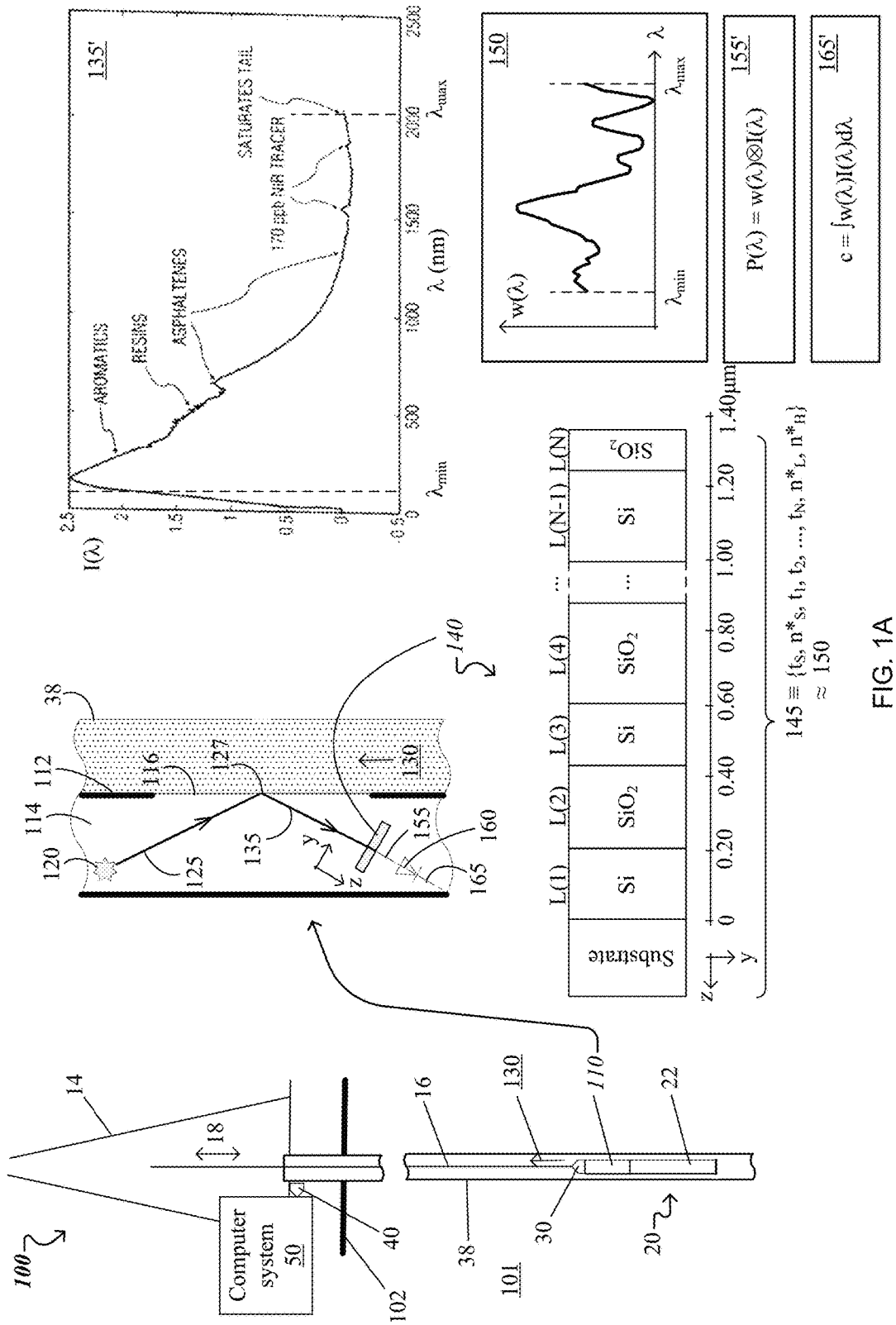

FIGS. 1A-1C show multiple configurations 100, 100', 100" of an example of a system for analyzing wellbore fluids 130, such that analyses are generated from measurements taken with a well logging tool 110 configured as an ICE-based optical analysis tool. The disclosed system also is referred to as a well logging system.

Each of the configurations 100, 100', 100" of the well logging system illustrated in FIGS. 1A-1C includes a rig 14 above the ground surface 102 and a wellbore 38 below the ground surface. The wellbore 38 extends from the ground surface into the earth 101 and generally passes through multiple geologic formations. In general, the wellbore 38 can contain wellbore fluids 130. The wellbore fluids 130 can be crude petroleum, mud, water or other substances and combinations thereof. Moreover, the wellbore fluids 130 may be at rest, or may flow toward the ground surface 102, for instance. Additionally, surface applications of the well logging tool 110 may include water monitoring and gas and crude transportation and processing.

FIG. 1A shows a configuration 100 of the well logging system which includes a tool string 20 attached to a cable 16 that can be lowered or raised in the wellbore 38 by draw works 18. The tool string 20 includes measurement and/or logging tools to generate and log information about the wellbore fluids 130 in the wellbore 38. In the configuration 100 of the well logging system, this information can be generated as a function of a distance (e.g., a depth) with respect to the ground surface 102. In the example illustrated in FIG. 1A, the tool string 20 includes the well logging tool 110, one or more additional well logging tool(s) 22, and a telemetry transmitter 30. Each of the well logging tools 110 and 22 measures one or more characteristics of the wellbore fluids 130. In some implementations, the well logging tool 110 determines values of the one or more characteristics in real time and reports those values instantaneously as they occur in the flowing stream of wellbore fluids 130, sequentially to or simultaneously with other measurement/logging tools 22 of the tool string 20.

FIG. 1B shows another configuration 100' of the well logging system which includes a drilling tool 24 attached to a drill string 16'. The drilling tool 24 includes a drill bit 26, the ICE-based well logging tool 110 configured as a measurement while drilling (MWD) and/or logging while drilling (LWD) tool, and the telemetry transmitter 30. Drilling mud is provided through the drill string 16' to be injected into the borehole 38 through ports of the drill bit 26. The injected drilling mud flows up the borehole 38 to be returned above the ground level 102, where the returned drilling mud can be resupplied to the drill string 16' (not shown in FIG. 1B). In this case, the MWD/LWD-configured well logging tool 110 generates and logs information about the wellbore fluids 130 (e.g., drilling mud in this case) adjacent the working drill bit 26.

FIG. 1C shows yet another configuration 100" of the well logging system which includes a permanent installation adjacent to the borehole 38. In some implementations, the permanent installation is a set of casing collars that reinforce the borehole 38. In this case, a casing collar 28 from among the set of casing collars supports the well logging tool 110 and the telemetry transmitter 30. In this manner, the well logging tool 110 determines and logs characteristics of the wellbore fluids 130 adjacent the underground location of the casing collar 28.

In each of the above configurations 100, 100' and 100" of the well logging system, the values of the one or more characteristics measured by the well logging tool 110 are provided (e.g., as a detector signal 165) to the telemetry transmitter 30. The latter communicates the measured values to a telemetry receiver 40 located above the ground surface 102. The telemetry transmitter 30 and the telemetry receiver 40 can communicate through a wired or wireless telemetry channel. In some implementations of the system configurations 100, 100' illustrated in FIGS. 1A and 1B, e.g., in slickline or coiled tubing applications, measurement data generated by the well logging tool 110 can be written locally to memory of the well logging tool 110.

The measured values of the one or more characteristics of the wellbore fluids 130 received by the telemetry receiver 40 can be logged and analyzed by a computer system 50 associated with the rig 14. In this manner, the measurement values provided by the well logging tool 110 can be used to generate physical and chemical information about the wellbore fluids 130 in the wellbore 38.

Referring again to FIG. 1A, the well logging tool 110 includes a light source 120, an ICE 140 and an optical transducer 160. The well logging tool 110 has a frame 112 such that these components are arranged in an enclosure 114 thereof. A cross-section of the well logging tool 110 in a plane perpendicular to the page can vary, depending on the space available. For example, the well logging tool's cross-section can be circular or rectangular, for instance. The well logging tool 110 directs light to the sample 130 through an optical interface 116, e.g., a window in the frame 112. The well logging tool 110 is configured to probe the sample 130 (e.g., the wellbore fluids stationary or flowing) in the wellbore 38 through the optical interface 116 and to determine an amount (e.g., a value) of a given characteristic (also referred to as a characteristic to be measured) of the probed sample 130. The characteristic to be measured can be any one of multiple characteristics of the sample 130 including concentration of a given substance in the sample, a gas-oil-ratio (GOR), pH value, density, viscosity, etc.

The light source 120 outputs light with a source spectrum over a particular wavelength range, from a minimum wavelength $\lambda_{min}$ to a maximum wavelength $\lambda_{max}$. In some implementations, the source spectrum can have non-zero intensity over the entire or most of the wavelength range $\lambda_{max}-\lambda_{min}$. In some implementations, the source spectrum extends through UV-vis (0.2-0.8 µm) and near-IR (0.8-2.5 µm) spectral ranges. Alternatively, or additionally, the source spectrum extends through near-IR and mid-IR (2.5-25 µm) spectral ranges. In some implementations, the source spectrum extends through near-IR, mid-IR and far-IR (25-100 µm) spectral ranges. In some implementations, the light source 120 is tunable and is configured in combination with time resolved signal detection and processing.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The light modified by the sample has a modified spectrum I(λ) 135' over the particular wavelength range. In the reflective configuration of the well logging tool 110 illustrated in FIG. 1A (i.e., where the light to be analyzed reflects at the sample/window interface), the modified spectrum I(λ) 135' is a reflection spectrum associated with the sample 130. In a transmission configuration of the well logging tool 110 (not shown in FIG. 1A), the probe beam is transmitted through the sample as modified light, such that the modified spectrum I(λ) 135' is a transmission spectrum associated with the sample.

In general, the modified spectrum I(λ) 135' encodes information about multiple characteristics associated with the sample 130, and more specifically the encoded information relates to current values of the multiple characteristics. In the example illustrated in FIG. 1A, the modified spectrum 135' contains information about one or more characteristics of the wellbore fluids 130.

With continued reference to FIG. 1A, and the Cartesian coordinate system provided therein for reference, the ICE 140 is arranged to receive a beam 135 of the sample modified light, and is configured to process it and to output a beam 155 of processed light. The beam 135 of sample modified light is incident on a first surface of the ICE 140 along the z-axis, and the beam 155 of processed light is output along the z-axis after transmission through the ICE 140. Alternatively or additionally, the beam 155 (or an additional reflected beam) of processed light can be output after reflection off the first surface of the ICE 140. The ICE 140 is configured to process the sample modified light by weighting it in accordance with an optical spectrum w(λ) 150 associated with a characteristic to be measured.

The optical spectrum w(λ) 150 is determined offline by applying conventional processes to a set of calibration spectra I(λ) of the sample which correspond to respective known values of the characteristic to be measured. As illustrated by optical spectrum w(λ) 150, optical spectrums generally may include multiple local maxima (peaks) and minima (valleys) between $\lambda_{min}$ and $\lambda_{max}$. The peaks and valleys may have the same or different amplitudes. For instance, an optical spectrum w(λ) can be determined through regression analysis of $N_c$ calibration spectra $I_j(\lambda)$ of a sample, where j=1, . . . , $N_c$, such that each of the calibration spectra $I_j(\lambda)$ corresponds to an associated known value of a given characteristic for the sample. A typical number $N_c$ of calibration spectra $I_j(\lambda)$ used to determine the optical spectrum w(λ) 150 through such regression analysis can be $N_c$=10, 40 or 100, for instance. The regression analysis outputs, within the $N_c$ calibration spectra $I_j(\lambda)$, a spectral pattern that is unique to the given characteristic. The spectral pattern output by the regression analysis corresponds to the optical spectrum w(λ) 150. In this manner, when a value of the given characteristic for the sample is unknown, a modified spectrum $I_u(\lambda)$ of the sample is acquired by interacting the probe beam 125 with the sample 130, then the modified spectrum $I_u(L)$ is weighted with the ICE 140 to determine a magnitude of the spectral pattern corresponding to the optical spectrum w(λ) 150 within the modified spectrum $I_u(\lambda)$. The determined magnitude is proportional to the unknown value of the given characteristic for the sample.

For example, the sample can be a mixture (e.g., the wellbore fluid 130) containing substances X, Y and Z, and the characteristic to be measured in the mixture is concentration $c_X$ of substance X in the mixture. In this case, $N_c$ calibration spectra $I_j(\lambda)$ were acquired for $N_c$ samples of the mixture having respectively known concentration values for each of the substances contained in the $N_c$ samples. By applying regression analysis to the $N_c$ calibration spectra $I_j(\lambda)$, a first spectral pattern that is unique to the concentration $c_X$ of the X substance can be detected (recognized), such that the first spectral pattern corresponds to a first optical spectrum $w_{cX}(\lambda)$ associated with a first ICE, for example. Similarly, second and third spectral patterns that are respectively unique to concentrations $c_Y$ and $c_Z$ of the Y and Z substances can also be detected, such that the second and third spectral patterns respectively correspond to second and third optical spectra $w_{cY}(\lambda)$ and $w_{cZ}(\lambda)$ respectively associated with second and third ICEs. In this manner, when a new sample of the mixture (e.g., the wellbore fluid 130) has an unknown concentration $c_X$ of the X substance, for instance, a modified spectrum $I_u(\lambda)$ of the new sample can be acquired by interacting the probe beam with the mixture, then the modified spectrum Iu(λ) is weighted with the first ICE to determine a magnitude of the first spectral pattern within the modified spectrum $I_u(\lambda)$. The determined magnitude is proportional to the unknown value of the concentration $c_X$ of the X substance for the new sample.

Referring again to FIG. 1A, the ICE 140 includes N layers of materials stacked on a substrate, such that complex refractive indices of adjacent layers are different from each other. The total number of stacked layers can be between 6 and 50, for instance. The substrate material can be BK7, diamond, Ge, ZnSe (or other transparent dielectric material), and can have a thickness in the range of 0.02-2 mm, for instance, to insure structural integrity of the ICE 140.

Throughout this specification, a complex index of refraction (or complex refractive index) n* of a material has a complex value, Re(n*)+iIm(n*). Re(n*) represents a real component of the complex index of refraction responsible for refractive properties of the material, and Im(n*) represents an imaginary component of the complex index of refraction (also known as extinction coefficient K) responsible for absorptive properties of the material. In this specification, when it is said that a material has a high complex index of refraction $n^*_H$ and another material has a low complex index of refraction $n^*_L$, the real component $Re(n^*_H)$ of the high complex index of refraction $n^*_H$ is larger than the real component $Re(n^*_L)$ of the low complex index of refraction $n^*_L$, $Re(n^*_H) > Re(n^*_L)$. Materials of adjacent layers of the ICE are selected to have a high complex index of refraction $n^*_H$ (e.g., Si), and a low complex index of refraction $n^*_L$ (e.g., $SiO_2$). Here, $Re(n^*_{Si}) \approx 2.4 > Re(n^*_{SiO2}) \approx 1.5$. For other material pairings, however, the difference between the high complex refractive index $n^*_H$ and low complex refractive index $n^*_L$ may be much smaller, e.g., $Re(n^*_H) \approx 1.6 > Re(n^*_L) \approx 1.5$. The use of two materials for fabricating the N layers is chosen for illustrative purposes only. For example, a plurality of materials having different complex indices of refraction, respectively, can be used. Here, the materials used to construct the ICE are chosen to achieve a desired optical spectrum w(λ) 150.

A set of design parameters 145—which includes the total number of stacked layers N, the complex refractive indices $n^*_H$, $n^*_L$ of adjacent stacked layers, and the thicknesses of the N stacked layers t(1), t(2), . . . , t(N−1), t(N)—of the ICE 140 can be chosen (as described below in connection with FIG. 2) to be spectrally equivalent to the optical spectrum w(λ) 150 associated with the characteristic to be measured. As such, an ICE design includes a set 145 of thicknesses {t(i), i=1, . . . , N} of the N layers stacked on the substrate that correspond to the optical spectrum w(λ) 150.

In view of the above, the beam 155 of processed light output by the ICE 140 has a processed spectrum P(λ)=w(λ)⊗I(λ) 155' over the wavelength range $\lambda_{max}$–$\lambda_{min}$, such that the processed spectrum 155' represents the modified spectrum I(λ) 135' weighted by the optical spectrum w(λ) 150 associated with the characteristic to be measured.

The beam 155 of processed light is directed from the ICE 140 to the optical transducer 160, which detects the processed light and outputs an optical transducer signal 165. A value (e.g., a voltage) of the optical transducer signal 165 is a result of an integration of the processed spectrum 155' over the particular wavelength range and is proportional to the unknown value "c" 165' of the characteristic to be measured for the sample 130.

In some implementations, the well logging tool 110 can include a second ICE (not shown in FIG. 1A) associated with a second ICE design that includes a second set of thicknesses {t'(i), i=1, . . . , N'} of a second total number N' of layers, each having a different complex refractive index from its adjacent layers, the complex refractive indices and the thicknesses of the N' layers corresponding to a second optical spectrum w'(λ). Here, the second optical spectrum w'(λ) is associated with a second characteristic of the sample 130, and a second processed spectrum represents the modified spectrum I(λ) 135' weighted by the second optical spectrum w'(λ), such that a second value of a second detector signal is proportional to a value of the second characteristic for the sample 130.

In some implementations, the determined value 165' of the characteristic to be measured can be logged along with a measurement time, geo-location, and other metadata, for instance. In some implementations, the detector signal 165, which is proportional to a characteristic to be measured by the well logging tool 110, can be used as a feedback signal to adjust the characteristic of the sample, to modify the sample or environmental conditions associated with the sample, as desired.

Characteristics of the wellbore fluids 130 that can be related to the modified spectrum 135' through the optical spectra associated with the ICE 140 and other ICEs (not shown in FIG. 1A) are concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

(2) Aspects of ICE Design

Aspects of a process for designing an ICE associated with a characteristic to be measured (e.g., one of the characteristics enumerated above) are described below. Here, an input of the ICE design process is a theoretical optical spectrum $w_{th}(\lambda)$ associated with the characteristic. An output of the ICE design process is an ICE design that includes specification of (1) a substrate and a number N of layers to be formed on the substrate, each layer having a different complex refractive index from its adjacent layers; and (2) complex refractive indices and thicknesses of the substrate and layers that correspond to a target optical spectrum $w_t(\lambda)$. The target optical spectrum $w_t(\lambda)$ is different from the theoretical optical spectrum $w_{th}(\lambda)$ associated with the characteristic, such that the difference between the target and theoretical optical spectra cause degradation of a target performance relative to a theoretical performance of the ICE within a target error tolerance. The target performance represents a finite accuracy with which an ICE having the target optical spectrum $w_t(\lambda)$ is expected to predict known values of the characteristic corresponding to a set of validation spectra of a sample with a finite (non-zero) error. Here, the predicted values of the characteristic are obtained through integration of the validation spectra of the sample respectively weighted by the ICE with the target optical spectrum $w_t(\lambda)$. The theoretical performance represents the maximum accuracy with which the ICE—if it had the theoretical optical spectrum $w_{th}(\lambda)$—would predict the known values of the characteristic corresponding to the set of validation spectra of the sample. Here, the theoretically predicted values of the characteristic would be obtained through integration of the validation spectra of the sample respectively weighted by the ICE, should the ICE have the theoretical optical spectrum $w_{th}(\lambda)$.

Figure 2A:
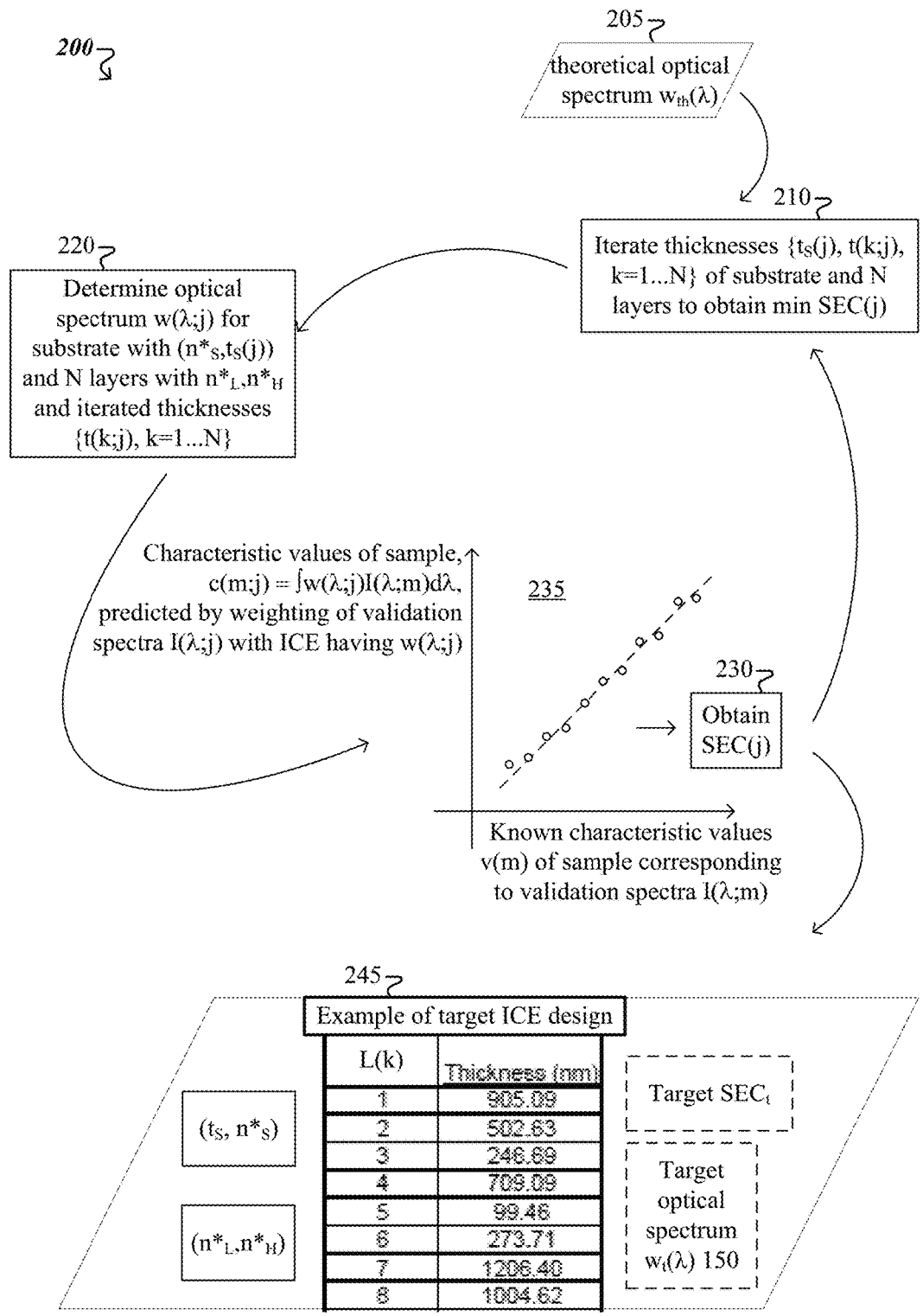
FIG. 2A is a flowchart showing an example of a process for designing an ICE.

FIG. 2A is a flow chart of an example of a process 200 for generating an ICE design. One of the inputs to the process 200 is a theoretical optical spectrum $w_{th}(\lambda)$ 205. For instance, to design an ICE for measuring concentration of a substance X in a mixture, a theoretical optical spectrum $w_{th}(\lambda)$, associated with the concentration of the substance X in the mixture, is accessed, e.g., in a data repository. As described above in this specification, the accessed theoretical optical spectrum $w_t(\lambda)$ corresponds to a spectral pattern detected offline, using a number $N_c$ of calibration spectra of the mixture, each of the $N_c$ calibration spectra corresponding to a known concentration of the substance X in the mixture. An additional input to the process 200 is a specification of materials for a substrate and ICE layers. Materials having different complex refractive indices, respectively, are specified such that adjacent ICE layers are formed from materials with different complex refractive indices. For example, a first material (e.g., Si) having a high complex refractive index $n^*_H$ and a second material (e.g., $SiO_x$) having a low complex refractive index $n^*_L$ are specified to alternately form the ICE layers. As another example, a layer can be made from high index material (e.g., Si), followed by a layer made from low index material (e.g., $SiO_x$), followed by a layer made from a different high index material (e.g., Ge), followed by a layer made from a different low index material ($MgF_2$), etc. The iterative design process 200 is performed in the following manner.

At 210 during the $j^{th}$ iteration of the design process 200, thicknesses {$t_S(j)$, t(1;j), t(2;j), . . . , t(N−1;j), t(N;j)} of the substrate and a number N of layers of the ICE are iterated.

At 220, a $j^{th}$ optical spectrum w(λ;j) of the ICE is determined corresponding to complex refractive indices and previously iterated thicknesses {$t_S(j)$, t(1;j), t(2;j), . . . , t(N−1;j), t(N;j)} of the substrate and the N layers, each having a different complex refractive index from its adjacent layers. The iterated thicknesses of the substrate and the N layers are used to determine the corresponding $j^{th}$ optical spectrum w(λ;j) of the ICE in accordance with conventional techniques for determining spectra of thin film interference filters.

At 230, performance of the ICE, which has the $j^{th}$ optical spectrum $w(\lambda;j)$ determined at 220, is obtained. To do so, a set of validation spectra of a sample is accessed, e.g., in a data repository. Respective values of a characteristic of the sample are known for the validation spectra. For instance, each of $N_v$ validation spectra $I(\lambda;m)$ corresponds to a value $v(m)$ of the characteristic of the sample, where $m=1, \ldots, N_v$. In the example illustrated in FIG. 2, $N_v=11$ validation spectra, respectively corresponding to 11 known values of the characteristic to be measured for the sample, are being used.

Graph 325 shows (in open circles) values $c(m;j)$ of the characteristic of the sample predicted by integration of the validation spectra $I(\lambda;m)$ weighted with the ICE, which has the $j^{th}$ optical spectrum $w(\lambda;j)$, plotted against the known values $v(m)$ of the characteristic of the sample corresponding to the validation spectra $I(\lambda;m)$. The predicted values $c(m;1)$ of the characteristic are found by substituting, in formula 165' of FIG. 1A, (1) the spectrum $I(\lambda)$ 135' of sample modified light with the respective validation spectra $I(\lambda;m)$ and (2) the target spectrum $w_t(\lambda)$ 150 with the $j^{th}$ optical spectrum $w(\lambda;j)$. In this example, performance of the ICE, which has the $j^{th}$ optical spectrum $w(\lambda;j)$, is quantified in terms of a weighted measure of distances from each of the open circles in graph 325 to the dashed-line bisector between the x and y axes. This weighted measure is referred to as the standard calibration error (SEC) of the ICE. For instance, an ICE having the theoretical spectrum $w_{th}(\lambda)$ has a theoretical $SEC_{th}$ that represents a lower bound for the $SEC(j)$ of the ICE having the $j^{th}$ spectrum $w(\lambda;j)$ determined at 220 during the $j^{th}$ iteration of the design process 200: $SEC(j) > SEC_{th}$.

In this specification, the SEC is chosen as a metric for evaluating ICE performance for the sake of simplicity. Note that there are other figures of merit that may be used to evaluate performance of ICE, as is known in the art. For example, sensitivity—which is defined as the slope of characteristic change as a function of signal strength—can also be used to evaluate ICE performance. As another example, standard error of prediction (SEP)—which is defined in a similar manner to the SEC except it uses a different set of validation spectra—can be used to evaluate ICE performance. Any of the figure(s) of merit known in the art is/are evaluated in the same general way by comparing theoretical performance with that actually achieved. Which figure(s) of merit or combinations are used to evaluate ICE performance is determined by the specific ICE design.

The iterative design process 200 continues by iterating, at 210, the thicknesses of the substrate and the N layers. The iterating is performed such that a $(j+1)^{th}$ optical spectrum $w(\lambda;j+1)$—determined at 220 from the newly iterated thicknesses—causes, at 230, improvement in performance of the ICE, to obtain $SEC(j+1) < SEC(j)$. In some implementations, the iterative design process 200 is stopped when the ICE's performance reaches a local maximum, or equivalently, the SEC of the ICE reaches a local minimum. For example, the iterative process 200 can be stopped at the $(j+1)^{th}$ iteration when the current $SEC(j+1)$ is larger than the last $SEC(j)$, $SEC(j+1) > SEC(j)$. In some implementations, the iterative design process 200 is stopped when, for a given number of iterations, the ICE's performance exceeds a specified threshold performance for a given number of iterations. For example, the iterative design process 200 can be stopped at the $j^{th}$ iteration when three consecutive SEC values decrease monotonously and are less than a specified threshold value: $SEC_0 > SEC(j-2) > SEC(j-1) > SEC(j)$.

In either of these cases, an output of the iterative process 200 represents a target ICE design 245 to be used for fabricating an ICE 140, like the one described in FIG. 1A, for instance. The ICE design 245 includes specification of (1) a substrate and N layers, each having a different complex refractive index from its adjacent layers, and (2) complex refractive indices $n^*_S$, $n^*_H$, $n^*_L$ and thicknesses $\{t_S(j), t(1;j), t(2;j), \ldots, t(N-1;j), t(N;j)\}$ of the substrate and N layers corresponding to the $j^{th}$ iteration of the process 200. Additional components of the ICE design are the optical spectrum $w(\lambda;j)$ and the $SEC(j)$—both determined during the $j^{th}$ iteration based on the thicknesses $\{t_S(j), t(1;j), t(2;j), \ldots, t(N-1;j), t(N;j)\}$. As the ICE design 245 is used as input for fabrication processes described herein, the iteration index j—at which the iterative process 200 terminates—is dropped from the notations used for the components of the ICE design.

In this manner, the thicknesses of the substrate and the N layers associated with the ICE design 245 are denoted $\{t_S, t(1), t(2), \ldots, t(N-1), t(N)\}$ and are referred to as the target thicknesses. The optical spectrum associated with the ICE design 245 and corresponding to the target thicknesses is referred to as the target optical spectrum $w_t(\lambda)$ 150. The SEC associated with the ICE design 245—obtained in accordance with the target optical spectrum $w_t(\lambda)$ 150 corresponding to the target thicknesses—is referred to as the target $SEC_t$. In the example illustrated in FIG. 2, the ICE design 245 has a total of $N=8$ alternating Si and $SiO_2$ layers, with complex refractive indices $n_{Si}$, $n_{SiO2}$, respectively. The layers' thicknesses (in nm) are shown in the table. An ICE fabricated based on the example of ICE design 245 illustrated in FIG. 2 is used to predict value(s) of concentration of substance X in wellbore fluids 130.

(3) Analysis of Sensitivity to Fabrication for ICE Design

Additionally, aspects of an analysis for determining a subset of critical layers, from among the N layers of the ICE design 245, are described below. A layer of the ICE design 245 is identified, by the analysis, to be a critical layer if potential variations of its complex refractive index and thickness—due to expected variations of a process for fabricating the layer—cause degradation from a target performance of the ICE within a predetermined error tolerance. In this example, the target performance represents the accuracy with which the ICE fabricated in accordance with the ICE design 245 is expected to predict the known values $v(m)$ of a characteristic corresponding to the set of validation spectra $I(\lambda;m)$ of the sample. Here, the predicted values $c(m)$ of the characteristic are obtained through integration of the validation spectra $I(\lambda;m)$ of the sample respectively weighted by the ICE. As noted above, other figures of merit that may be used to represent performance of the ICE, as is known in the art. For example, sensitivity—which is defined as the slope of characteristic change as a function of signal strength—can also be used to represent the ICE performance.

For example, a layer from among the N layers of the ICE can be erroneously formed with an off-target thickness, an off-target complex refractive index, or a combination of off-target thickness and complex refractive index. Such complex refractive index or thickness errors may cause a shift or a change in the optical spectrum of the fabricated ICE relative to the target optical spectrum $w_t(\lambda)$ 150. If the shifts and/or changes in the optical spectrum—even when they appear to be large—are caused by off-target complex refractive index or thickness of a noncritical ICE layer, only insignificant degradation in performance of the fabricated ICE relative to the target performance may occur. In such cases, the SEC of the fabricated ICE may stay the same or increase only slightly (e.g., by less than 10%) relative to the target SEC. However, if the shifts and/or changes in the optical spectrum—even when they appear to be small—are caused by off-target complex refractive index or thickness of a critical ICE layer, significant degradation in performance of the fabricated ICE relative to the target performance may occur. In the latter cases, the SEC of the fabricated ICE may greatly increase (e.g., by more than 20%, 50% or even 100%) relative to the target SEC.

Figure 2B:
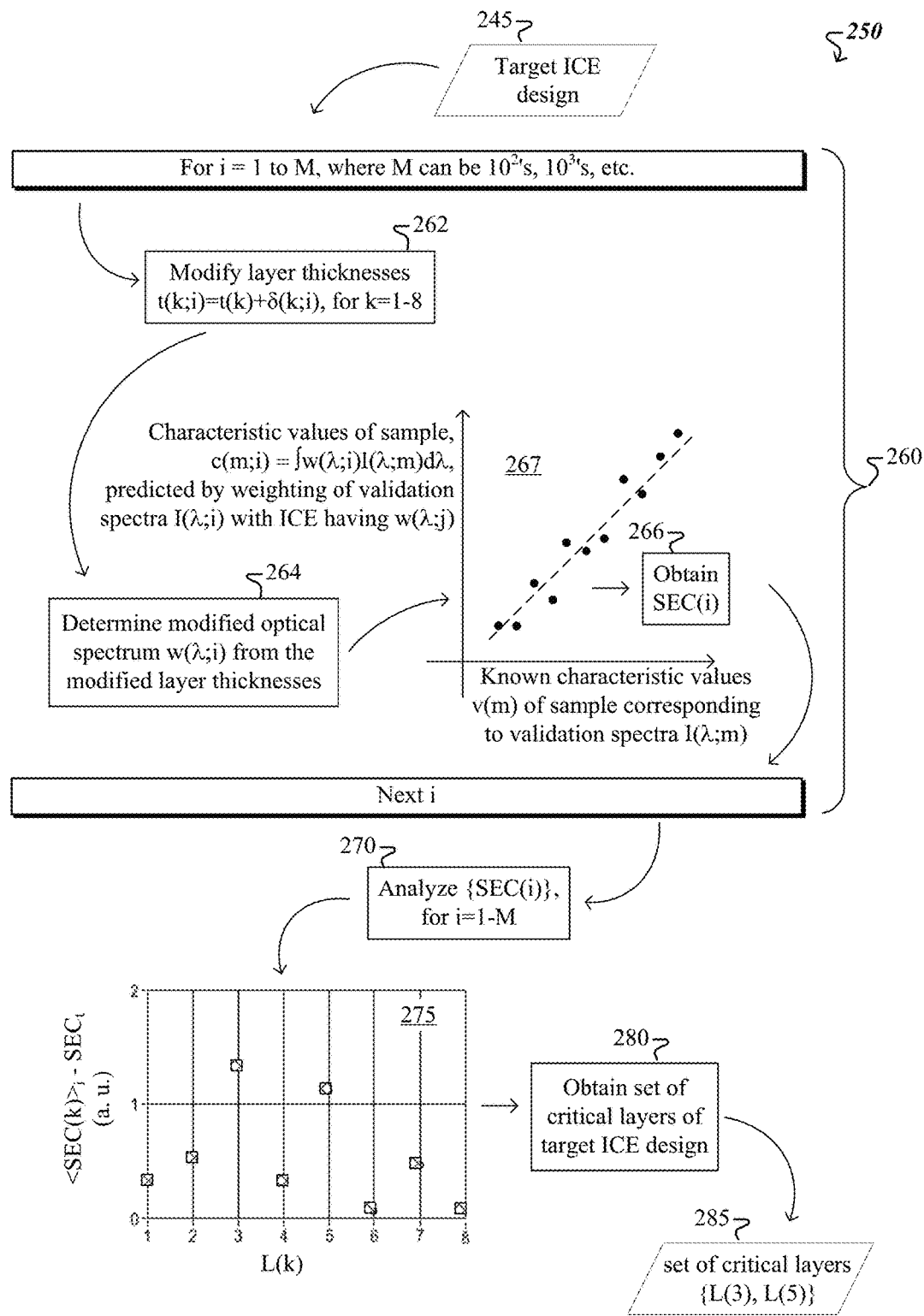
FIG. 2B is a flowchart showing an example of a process for determining critical layers of an ICE design.

FIG. 2B is a flow chart of an example of an analysis 250 for determining a subset of critical layers of an ICE design. The input ICE design 245 includes specification of a substrate and N layers L(1), L(2), ..., L(N), each having a different complex refractive index from its adjacent layers, and specification of target complex refractive indices and thicknesses $t_S$, t(1), t(2), ..., t(N). In this example, N=8 and materials of adjacent layers are Si and $SiO_2$. Additionally, the specification of the ICE design 245 includes, explicitly or implicitly, a target optical spectrum $w_t(\lambda)$ 150, a target $SEC_t$, or both.

Loop 260 is used to generate a number M of modified ICE designs starting from the target ICE design 245. A large number M of modified ICE designs can be generated in this manner, for example, hundreds, thousands, tens of thousands, or more modified ICE designs. In some implementations, the sequence of operations 262, 264 and 266 within the loop 260 is executed for the $i^{th}$ modified ICE design after this operation sequence has been completed for the $(i-1)^{th}$ modified ICE design, and will be completed before starting execution of this operation sequence for the $(i+1)^{th}$ modified ICE design. This represents an iterative (or sequential) mode for executing the loop 260. In some implementations, the sequence of operations 262, 264 and 266 within the loop 260 is executed in parallel for all $1^{st}, 2^{nd}, \ldots, i^{th}, \ldots, (M-1)^{th}$, $M^{th}$ modified ICE designs. This represents a branch (or parallel) mode for executing the loop 260. In some other implementations, some of the M modified ICE designs are processed sequentially, and the remaining ones in parallel. The $i^{th}$ modification of the target design 245 through the loop 260 is described below as it is executed in either of the sequential mode or the parallel mode.

At 262, thicknesses of the N layers of target ICE design 245 are modified to obtain the $i^{th}$ modified ICE design. For each of the layers L(k), k=1, ..., N, of the target ICE design 245, its target thickness t(k) is changed by a value δ(k;i) to obtain a modified thickness t(k;i)=t(k)+δ(k;i). A positive thickness change δ(k;i)>0 corresponds to a modified thickness t(k;i) of the layer L(k) that is thicker than its target thickness t(k), while a negative thickness change δ(k;i)<0 corresponds to a modified thickness t(k;i) of the layer L(k) that is thinner than its target thickness t(k). For instance, magnitudes of the thickness changes correspond to potential thickness errors caused by known or expected variations of an ICE fabrication process. The variations in the ICE fabrication process can be caused by changes in deposition rate, changes in distance between deposition source(s) and ICE substrate(s), changes in deposition chamber temperature and/or pressure, changes in chemical composition of deposition source materials, and more.

The $i^{th}$ modified ICE design can include modification of a single layer from among the N layers, or modifications of a few, most or all of the N layers. In some implementations, the thickness changes δ(k;i) of at least some of the N layers corresponding to the $i^{th}$ modified ICE design are random values. For example, the thickness changes δ(p;1), δ(p;2), ..., δ(p;M-1), δ(p;M) of a $p^{th}$ layer of the $1^{st}, 2^{nd}, \ldots, (N-1)^{th}, N^{th}$ modified ICE designs are random values. As another example, the thickness changes δ(k;i) of at least some of the N layers of the $i^{th}$ modified ICE design are predetermined values. In some implementations, the thickness changes δ(p;1), δ(p;2), ..., δ(p;M-1), δ(p;M) of a $p^{th}$ layer corresponding to the $1^{st}, 2^{nd}, \ldots, (N-1)^{th}, N^{th}$ modified ICE designs have predetermined values. The predetermined values can be ±5 nm, ±10 nm, ±50 nm, ±100 nm, etc.

At 264, an $i^{th}$ modified optical spectrum w(λ;i) associated with the $i^{th}$ modified ICE design is determined Conventional techniques for determining spectra of thin film interference filters can be used to determine the $i^{th}$ modified optical spectrum w(λ;i) based, at least in part, on the modified layer thicknesses t(k;i)=t(k)+δ(k;i), where k=1, ..., N, of the $i^{th}$ modified ICE design.

At 266, degradation from a target performance of an ICE associated with the $i^{th}$ modified ICE design is obtained. Here, graph 267 shows (in full circles) values c(m;i) of the characteristic of the sample predicted by weighting the validation spectra I(λ;m) with an ICE associated with the $i^{th}$ modified ICE design plotted against the known values v(m) of the characteristic of the sample corresponding to the validation spectra I(λ;m). For the $i^{th}$ modified ICE design, the predicted values c(m;i) of the characteristic are found by substituting, in formula 165' of FIG. 1A, (1) the spectrum I(λ) 135' of sample modified light with the respective validation spectra I(λ;m) and (2) the target optical spectrum $w_t(\lambda)$ 150 with the $i^{th}$ modified optical spectrum w(λ;i) determined at 264. Once again, performance of the ICE having the $i^{th}$ modified optical spectrum w(λ;i) is quantified in terms of a weighted measure of distances from each of the full circles in graph 267 to the dashed-line bisector between the x and y axes. This weighted measure is the SEC(i) of the ICE associated with the $i^{th}$ modified ICE design. In this manner, the SEC(i) of the ICE associated with the $i^{th}$ modified ICE design is a measure of this ICE's degradation with respect to performance of the ICE associated with the target design 245.

An output of the loop 260 is a set {SEC(i), i=1-M} of measures of performance degradations of M ICEs respectively associated with the M modified ICE designs generated by the loop 260.

At 270, the set {SEC(i), i=1-M} of measures of performance degradations of the M ICEs—respectively associated with the M modified ICE designs generated by the loop 260—is analyzed. As described above, each of the SEC(i) in the analyzed set corresponds to an $i^{th}$ modification of the layer thicknesses t(k;i)=t(k)+δ(k;i), where k=1, ..., N. The analysis performed at 270 determines contributions to performance degradation SEC(i) of the $i^{th}$ modified ICE design caused by respective changes in thickness δ(k;i) associated with each of the layers L(k). For instance, this analysis determines a first contribution SEC(i;1) caused by changes in thickness δ(1;i) associated with the $1^{st}$ layer L(1), a second contribution SEC(i;2) caused by changes in thickness δ(2;i) associated with the $2^{nd}$ layer L(2), ..., and an $N^{th}$ contribution SEC(i;N) caused by changes in thickness δ(N;i) associated with the $N^{th}$ layer L(N).

A global influence on ICE performance degradation by each layer L(k) (where k=1-N), over all $i^{th}$ modified ICE designs (where i=1-M), is found by calculating a statistic $<SEC(k)>_i$ of the determined layer-by-layer contributions. Examples of statistics that can be used here are averages, truncated averages, medians, sums or maximums of the contributions of a layer L(k) (where k=1–N) over all $i^{th}$ modified ICE designs (where i=1–M). For example, $<SEC(1)>_i=(1/M)\Sigma^M_{i=1}SEC(i;1)$ represents an average of contributions SEC(i;1) to performance degradation by the first layer L(1) taken over all $i^{th}$ modified ICE designs (where i=1–M); $<SEC(2)>_i=(1/M)\Sigma^M_{i=1}SEC(i;2)$ represents an average of contributions SEC(i;2) to performance degradation by the second layer L(2) taken over all $i^{th}$ modified ICE designs (where i=1–M); . . . ; and $<SEC(N)>_i=(1/M)\Sigma^M_{i=1}SEC(i;N)$ represents an average of contributions SEC(i;N) to performance degradation by the $N^{th}$ layer L(N) taken over all $i^{th}$ modified ICE designs (where i=1–M). Graph 275 shows average contributions $<SEC(\lambda)>_i$—caused by each layer L(k) of the N layers—to the performance degradation of the ICE design 245 relative to the target performance degradation. Target performance of this ICE can be specified as part of the target ICE design 245 as $SEC_t$. In the example shown in graph 275, the layer-by-layer average contributions to the ICE's performance degradation are plotted relative to the target performance Here, there are N=8 layers in the ICE design 245. For example, a value of 1.4 (in arbitrary units) for the average contribution $<SEC(3)>_i$ caused by layer L(3) to performance degradation relative to the target performance $SEC_t$ means that fabrication variances in the thickness of the third layer L(3) will potentially lead, on the average, to 1.4 (a.u.) of additional degradation on top of the expected degradation $SEC_t$. As another example, a value of 0.1 (a.u.) for the average contribution $<SEC(6)>_i$ caused by layer L(6) to performance degradation relative to the target performance $SEC_t$ means that the fabrication variances in the thickness of the sixth layer L(6) will potentially lead, on the average, to insignificant additional degradation (only 0.1 (a.u.)) on top of the expected degradation $SEC_t$.

At 280, a set 285 of critical layers of the target ICE design 245 is obtained. In some implementations, guidelines that depend on capability of fabrication equipment can be used to differentiate critical layers from non-critical layers. If an ICE associated with the target ICE design 245 were to be fabricated using fabrication equipment capable of performing low variability fabrication processes, a threshold for differentiating the critical from non-critical layers can be set to a high value. For example, in this case, only layers that cause an increase of performance degradation of more than 100% relative to the target performance degradation $SEC_t$ are considered to be critical layers, while the remaining layers are considered non-critical. However, if an ICE associated with the ICE design 245 were to be fabricated using fabrication equipment incapable of performing low variability fabrication processes, the threshold for differentiating the critical from non-critical layers can be set to a low value. For example, in this case, layers that cause an increase of performance degradation of more than 10% relative to the target performance degradation $SEC_t$ are considered to be critical layers, while the remaining layers would be considered non-critical. In some implementations, statistical guidelines can be used to differentiate critical layers from non-critical layers. For example, 25% of the N layers which cause the largest increases of performance degradation relative to the target performance degradation $SEC_t$ are considered to be critical layers, while the remaining 75% of the N layers are considered non-critical. In another example, layers that cause an increase of performance degradation of more than 100% relative to a median increase of performance degradation of all the N layers are considered to be critical layers, while the remaining layers are considered non-critical.

In the example illustrated in FIG. 2B, the sixth layer L(6) and the eight layer L(8) are predicted to be insensitive to variability in the fabrication process because they have a small contribution to performance degradation relative to the target performance $SEC_t$—in this case about 0.1 (a.u.). The first layer L(1), the second layer L(2), the fourth layer L(4) and the seventh layer L(7) are predicted to be somewhat more sensitive to variability in the fabrication process than the sixth layer L(6) and the eight layer L(8), because L(1), L(2), L(4) and L(7) have an intermediate contribution to performance degradation relative to the target performance $SEC_t$—in this case in the range of 0.2-0.6 (a.u.). Moreover, the third layer L(3) and the fifth layer L(5) are predicted to be most sensitive from among the 8 layers of the ICE design 245 to variability in the fabrication process, because L(3) and L(5) have a large contribution to performance degradation relative to the target performance degradation $SEC_t$—in this case larger than 1.2 (a.u.). For instance, the threshold for designating a critical layer can be set at 1 (a.u.). In this case, layers that cause an increase of performance degradation of more than 1 (a.u.) relative to the target performance degradation $SEC_t$ are considered to be critical layers. The remaining layers are considered non-critical, in this case. As such, the analysis 250 of the target ICE design 245, for the example illustrated in FIG. 2B, results in a set of critical layers {L(3), L(5)}.

(4) Technologies for Fabricating Critical Layer(s) of ICE

As described above in connection with FIG. 2A, an ICE design specifies a number of material layers, each having a different complex refractive index from its adjacent layers. An ICE fabricated in accordance with the ICE design has (i) a target optical spectrum $w_t(\lambda)$ and (ii) a target performance $SEC_t$, both of which corresponding to the complex refractive indices and target thicknesses of a substrate and a total number of layers specified by the ICE design. Performance of the ICE fabricated in accordance with the ICE design can be very sensitive to actual values of the complex refractive indices and thicknesses obtained during deposition. For a wide variety of reasons, the actual values of the complex refractive indices of materials to be deposited and/or the rate(s) of the deposition may drift within a fabrication batch or batch-to-batch, or may be affected indirectly by errors caused by measurement systems used to control the foregoing fabrication parameters. For example, materials used for deposition (Si, $SiO_2$) may be differently contaminated, or react differently due to different chamber conditions (e.g., pressure or temperature). It is expected, based on the analysis described above in connection with FIG. 2B, that performance of an ICE associated with an ICE design can be very sensitive to actual values of the complex refractive indices and thicknesses obtained during deposition. As such, for layers of the ICE design 245 identified by the analysis 250 as critical layers, a small error, e.g., 0.1% or 0.001%, in the thickness of a deposited critical layer can result in a reduction in the performance of an ICE associated with the ICE design 245 below an acceptable threshold.

Some conventional processes for fabricating optical thin films are generally turned to an "on" state for each layer to be deposited until that layer is complete. The "on" method is generally used and generally successful because the tolerances associated with the optical thicknesses of conventional thin film stacks are 1-5%, which is orders of magnitude higher than for ICE. In contrast, ICE design and operation requires point by point accuracies of <0.01% or more typically. Thus, an "on" fabrication process will almost always result in either undershoot or overshoot, especially for high speed thermal evaporation processes. The ICE fabrication disclosed below in this specification includes layer deposition processes that are interrupted (sometimes multiple times) prior to completion of the deposition of a layer. In this manner, determinations of the complex refractive index and thickness of the deposited layer can be performed, and corrections to the ICE design and/or deposition process made. Throughout this specification, determining a complex refractive index $n^*$ of a layer means that both the real component $Re(n^*)$ and the imaginary component $Im(n^*)$ of the complex refractive index are being determined.

A single layer of the specified number of layers of the ICE design may be deposited continuously (in a single step), in accordance with some conventional processes for fabricating optical thin films, until a desired layer thickness is achieved. In the case of high speed evaporation, for instance, a small error or miscalculation in deposition rate, e.g. 1%, can lead to depositing a layer with a thickness that is 0.1% (or in some cases 0.001%) too thick (or thin) relative to a target thickness, for instance. Although this would be a small error in the resulting thickness of a fabricated conventional thin film layer stack, the performance of a fabricated ICE can be reduced below an acceptable threshold due to the off-target resulting thickness. The disclosed technologies include fabricating at least a particular layer (e.g., one of the critical layers) from among the specified layers of an ICE in multiple deposition steps, such that each of the multiple steps is used to fabricate two or more sub-layers of the particular layer. The sub-layers are layers—within the particular single layer of material—that are deposited in the following manner: deposition of the particular layer is stopped when a sub-layer is completed; optical (e.g., complex refractive indices) or physical (e.g., thickness) characteristics of the completed sub-layer are measured using an optical measurement (e.g., one or more of ellipsometry, optical monitoring and spectroscopy) or a physical measurement (e.g., a physical monitor, such as a crystal microbalance) or both; then deposition of the particular layer restarts with deposition of the next sub-layer. The sub-layers are deposited such that the sum of their thicknesses, within the particular layer, is about equal to a thickness of the particular layer as specified by the ICE design. Moreover, results of the measurements performed after depositing a sub-layer are used to determine whether the deposition rate, chemical composition, or other fabrication parameters related to layer material deposition has changed during deposition of the sub-layer, and if so, to adjust one or more of these fabrication parameters to compensate for the determined change(s).

A potential advantage of depositing sub-layers is that particularly difficult or challenging layers of an ICE, e.g., thick or critical layers, can be more accurately deposited. For example, instead of depositing a (thick) layer to a target thickness of 400 nm in a single deposition step, four sub-layers can be deposited with a thickness of 100 nm each (still totaling 400 nm). Notably, the sub-layers can but need not have the same thickness. After each sub-layer is deposited, in situ diagnostics can be used to determine the actual thickness and/or complex refractive index achieved, and the design or fabrication of subsequent sub-layer(s) and layers may be modified appropriately. In this manner, a first sub-layer error of 5 nm, for instance, can be appropriately corrected by correspondingly increasing or decreasing a target thickness of one or more of sub-layers deposited next. In this manner, errors in deposition of any single layer are based only on a single error (the inherent error of the fabrication process) and are not additive, layer by layer.

When performance of an ICE design is modeled by introducing random variations in the thickness of each individual layer of the ICE, it can be shown (in accordance with the analysis 250 described above in connection with FIG. 2B) that some layers are far more susceptible to this variation. These sensitive layers of the ICE are more critical and important to the ICE's performance than other layers with respect to fabrication errors. For example, achieving a desired thickness (and/or complex refractive index) for a deposited critical layer may be more important to the ICE performance than achieving the desired thickness (and/or complex refractive index) of a deposited non-critical layer. The knowledge of which layers are most sensitive to the ICE performance can be used (1) to designate them as critical layers, and (2) to specify and deposit a suitable number of sub-layers for each of the layers designated as critical. Using "on" fabrication processes to deposit critical layers will almost always results in an ICE product whose performance is substandard, and thereby affects the yield, etc. Depositing sub-layers of a critical layer, in accordance with the disclosed technologies, enables accurate fabrication of that critical layer, which in turn contributes to accurate performance of the entire ICE.

Details of one or more of the foregoing embodiments are described below.

(4.1) System for Fabricating Critical Layer(s) of ICE

Once the critical layers of a target ICE design have been identified, this information can be provided to an ICE fabrication system in which one or more ICEs are fabricated based on the target ICE design. Technologies for selectively forming layers of the ICE device, in accordance with a designation of each of the layers as being either a critical layer or a non-critical layer are described below. For instance, each of the critical layers can be formed in two or more forming steps, and each of the non-critical layers can be formed in a single forming step. A fabrication system for implementing these technologies is described below.

Figure 3:
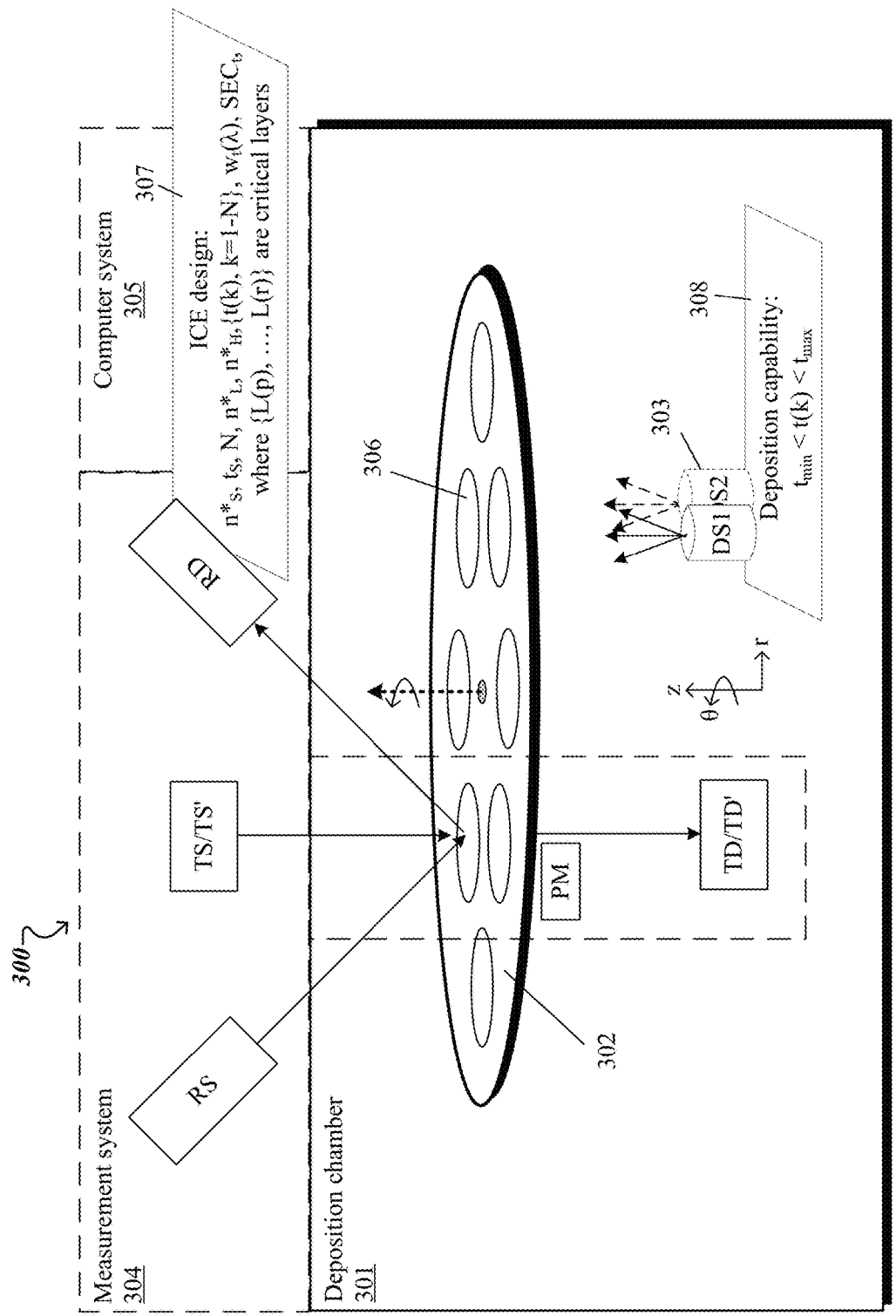
FIG. 3 shows an example of a system for fabricating one or more ICEs associated with an ICE design that specifies critical and non-critical layers.

FIG. 3 shows a schematic representation of an example of an ICE fabrication system 300. The ICE fabrication system 300 includes a deposition chamber 301 to fabricate one or more ICEs 306, a measurement system 304 to measure at least one characteristic of the ICE while it is being fabricated, and a computer system 305 to control the fabrication of the one or more ICEs 306 based at least in part on results of the measurements.

The deposition chamber 301 includes one or more deposition sources 303 to provide materials with a low complex index of refraction $n^*_L$ and a high complex index of refraction $n^*_H$ used to form layers of the ICEs 306. Substrates on which layers of the ICEs 306 will be deposited are placed on a substrate support 302, such that the ICEs 306 are within the field of view of the deposition source(s) 303. The substrates have a thickness $t_S$ and a complex refractive index $n^*_S$ specified by the ICE design 307. Various physical vapor deposition (PVD) techniques can be used to form a stack of layers of each of the ICEs 306 in accordance with a target ICE design 145 or 245, for instance. In accordance with PVD techniques, the layers of the ICE(s) are formed by condensation of a vaporized form of material(s) of the source(s) 305, while maintaining vacuum in the deposition chamber 301. One such example of PVD technique is electron beam (E-beam) deposition, in which a beam of high energy electrons is electromagnetically focused onto material(s) of the deposition source(s) 303, e.g., either Si, or $SiO_2$, to evaporate atomic species. In some cases, E-beam deposition is assisted by ions, provided by ion-sources (not shown in FIG. 3), to clean or etch the ICE substrate(s); and/or to increase the energies of the evaporated material(s), such that they are deposited onto the substrates more densely, for instance. Other examples of PVD techniques that can be used to form the stack of layers of each of the ICEs 306 are cathodic arc deposition, in which an electric arc discharged at the material(s) of the deposition source(s) 303 blasts away some into ionized vapor to be deposited onto the ICEs 306 being formed; evaporative deposition, in which material(s) included in the deposition source(s) 303 is(are) heated to a high vapor pressure by electrically resistive heating; pulsed laser deposition, in which a laser ablates material(s) from the deposition source(s) 303 into a vapor; or sputter deposition, in which a glow plasma discharge (usually localized around the deposition source(s) 303 by a magnet—not shown in FIG. 3) bombards the material(s) of the source(s) 303 sputtering some away as a vapor for subsequent deposition.

A relative orientation of and separation between the deposition source(s) 303 and the substrate support 302 are configured to provide desired deposition rate(s) and spatial uniformity across the ICEs 306 disposed on the substrate support 302. Additionally, the substrate support 302 is rotated about the deposition chamber 301 (e.g., about the deposition chamber 301's azimuthal axis) and relative to the deposition source(s) 303 to obtain reproducibly uniform layer deposition of all the ICEs 306 within a batch.

In some implementations, the ICE fabrication system 300 can be used to deposit layers that are no thinner than a minimum thickness, $t_{min}$. Here, layers formed to a target thickness that is less than $t_{min}$, would have non-uniform thicknesses, for instance. In some implementations, the ICE fabrication system 300 can be used to deposit layers that are no thicker than a maximum thickness, $t_{max}$. For instance, a deposition rate is constant, $R(t)=R_0$, when depositing layers with thicknesses up to this threshold thickness, $t \le t_{max}$, but may depend on the layer thickness, $R(t)=R_0+m \cdot t$, with $m \ne 0$, when depositing layers with thicknesses above this threshold thickness, $t > t_{max}$. As deposition of layers with a target thickness that exceeds $t_{max}$ is a non-linear deposition process, such non-linear deposition may be difficult to control. The thickness range $[t_{min}, t_{max}]$ represents an aspect 308 of the deposition capability of the ICE fabrication system 300. Moreover, this aspect 308 of the deposition capability can depend on material of the source 303, type of the source 303, relative distance and orientation between the source 303 and the substrate support 302, etc.

The measurement system 304 associated with the ICE fabrication system 300 includes one or more instruments. For example, a physical thickness monitor (e.g., a quartz crystal microbalance—not shown in FIG. 3) is used to measure a deposition rate, R. The measured deposition rate R is used to control power provided to the deposition source 303, its arrangement relative to the substrate support 302, etc. For instance, if an ICE design specifies that a $j^{th}$ layer L(j) of the N layers of an ICE is a Si layer with a target thickness t(j), a stack including the $(j-1)^{th}$ previously formed ICE layers is exposed to a Si source—from among the deposition sources 303—for a duration $\Delta T=t(j)/R_{Si}$, where the $R_{Si}$ is the measured deposition rate of the Si source. The measured deposition rate(s) R and the times used to deposit the formed layers L(1), L(2), . . . , L(j-1), L(j) can be used by the computer system 305 to determine actual values of the thicknesses t'(1), t'(2), . . . , t'(j-1), t'(j) of these layers.

Actual thickness of the formed layers L(1), L(2), . . . , L(j-1), L(j) also are determined from measurements of one or more characteristics of the formed layers. Such characteristics of the formed layers are measured with other instruments of the measurement system 304.

For example, an ellipsometer is used to measure, after forming the $j^{th}$ layer of the ICE 306, amplitude and phase components $(\Psi(j), \Delta(j))$ of elliptically polarized probe light provided by source RS after reflection from the stack with j layers of the ICE that is being formed in the deposition chamber 301. Note that probe-light represents any type of electromagnetic radiation having one or more probe wavelengths from an appropriate region of the electromagnetic spectrum. In this case, the probe light is provided by the source RS through a probe window of the deposition chamber 301 associated with the ellipsometer, and the reflected light is collected by a detector RD through a detector window of the deposition chamber 301 associated with the ellipsometer. Here, the measured amplitude and phase components $(\Psi(j), \Delta(j))$ can be used by the computer system 305 to determine the complex refractive indices and thicknesses of each of the formed layers in the stack: $n^{*'}_{Si}$, $n^{*'}_{SiO2}$, t'(1), t'(2), . . . , t'(j-1), t'(j). The computer system 305 makes this determination by solving Maxwell's equations for propagating the interacted probe-light through the formed layers in the stack.

As another example, a spectrometer is used to measure, after forming the $j^{th}$ layer of the ICE 306, a spectrum $S(j;\lambda)$ of light provided by a source TS over a broad wavelength range from $\lambda_{min}$, $\lambda_{max}$ after transmission through the stack with j layers of the ICE that is being formed in the deposition chamber 301. In this case, the broad wavelength range source TS provides light through a probe window of the deposition chamber 301 associated with the spectrometer, and a detector TD collects the transmitted light through a detector window of the deposition chamber 301 associated with the spectrometer. Here, the measured spectrum $S(j;\lambda)$, over the wavelength range from $\lambda_{min}$, $\lambda_{max}$, can be used by the computer system 305 to determine the complex refractive indices and thicknesses of each of the formed layers in the stack: $n^{*'}_{Si}$, $n^{*'}_{SiO2}$, t'(1), t'(2), . . . , t'(j-1), t'(j). The computer system 305 makes this determination by solving Maxwell's equations for propagating the interacted probe-light through the formed layers in the stack.

As yet another example, an optical monitor is used to measure, after forming the $j^{th}$ layer of the ICE 306, change of intensity $I(j;\lambda_k)$ of a probe light provided by source TS' due to transmission through the stack with j layers of the ICE that is being formed in the deposition chamber 301. The source of the optical monitor can be one and the same as the source of the spectrometer TS, which emits over a broad wavelength range, filtered with a filter centered on $\lambda_k$ having a narrow bandwidth $\Delta\lambda_k$, e.g., ±5 nm or less. Or the source of the optical monitor can be a different source TS' that emits one or more "discrete" wavelengths $\{\lambda_k, k=1, 2, \ldots\}$. A discrete wavelength $\lambda_k$ includes a center wavelength $\lambda_k$ within a narrow bandwidth $\Delta\lambda_k$, e.g., ±5 nm or less; two or more wavelengths, $\lambda_1$ and $\lambda_2$, contained in the probe-light have respective bandwidths $\Delta\lambda_1$ and $\Delta\lambda_2$ that are not overlapping. The source TS' can be a continuous wave (CW) laser, for instance. The source TS' provides, probe-light through a probe window of the deposition chamber 301 associated with the optical monitor and a detector TD' collects, through a detector window of the deposition chamber 301 associated with the optical monitor, the transmitted light with an intensity $I(j;\lambda_k)$. Here, the measured change of intensity $I(j;\lambda_k)$ can be used by the computer system 305 to determine the complex refractive indices and thicknesses of each of the formed layers in the stack: $n^*_{Si}$, $n^*_{SiO2}$, $t(1)$, $t(2), \ldots, t(j-1), t(j)$. The computer system 305 makes this determination by solving Maxwell's equations for propagating the interacted probe-light through the formed layers in the stack.

The computer system 305 includes one or more hardware processors and memory. The memory encodes instructions that, when executed by the one or more hardware processors, cause the fabrication system 300 to perform processes for fabricating the ICEs 306. Examples of such processes are described below in connection with FIGS. 4, 5A and 6A. The computer system 305 also includes or is communicatively coupled with a storage system that stores one or more ICE designs 307, aspects 308 of the deposition capability, and other information. The stored ICE designs can be organized in design libraries by a variety of criteria, such as ICE designs used to fabricate ICEs for determining values of a particular characteristic over many substances (e.g. the GOR ratio in crude oil, refined hydrocarbons, mud, etc.), or ICE designs used to fabricate ICEs for determining values of many properties of a given substance (e.g., viscosity, GOR, density, etc., of crude oil.) In this manner, upon receipt of an instruction to fabricate an ICE for measuring a given characteristic of a substance, the computer system 305 accesses such a design library and retrieves an appropriate ICE design 307 that is associated with the given characteristic of the substance.

The retrieved ICE design 307 includes specification of a substrate and a total number N of layers to be formed in the deposition chamber 301 on the substrate; specification of a complex refractive index $n_S$ of a material of the substrate, a high complex refractive index $n^*_H$ and a low complex refractive index $n^*_L$ of materials (e.g., Si and SiO$_2$) to form the N layers with adjacent layers having different complex refractive indices; and specification of target thicknesses $\{t_S, t(k), k=1-N\}$ of the N layers Implicitly or explicitly, the ICE design 307 also can include specification of a target optical spectrum $w_t(\lambda)$ associated with the given characteristic; and specification of a target SEC$_t$ representing expected performance of an ICE associated with the retrieved ICE design 307. The foregoing items of the retrieved ICE design 307 were determined, prior to fabricating the ICEs 306, in accordance with the ICE design process 200 described above in connection with FIG. 2A. In some implementations, the ICE design 307 can include indication of maximum allowed SEC$_{max}$ caused by fabrication errors. Figures of merit other than the target SEC$_t$ can be included in the retrieved ICE design 307, e.g., SEP, the ICE sensitivity, etc. Additionally, the ICE design 307 includes indication of a set of critical layers $\{L(p), \ldots, L(r)\}$ from among the N layers specified by the ICE design. The critical layers $\{L(p), \ldots, L(r)\}$ were determined, prior to fabricating the ICEs 306, in accordance with the analysis 250 for identifying critical layers of an ICE design, as described above in connection with FIG. 2B.

The complex refractive indices and target thicknesses $\{t(\lambda), k=1-N\}$ of the N layers, as specified by the retrieved ICE design 307, are used by the computer system 305, in conjunction with aspects 308 of deposition capability of the ICE fab system 300, to control deposition rate(s) of the deposition source(s) 303 and respective deposition times for forming the ICE layers. Identification of a layer of the retrieved ICE design 307 as a critical layer causes the computer system 305 to instruct the ICE fabrication system 300 to form the critical layer using multiple forming steps. In this manner, the multiple forming steps form respective sub-layers of the critical layer. If another layer of the retrieved ICE design 307 is not identified as a critical layer, the computer system 305 instructs the ICE fabrication system 300 to form the other ("non-critical") layer using a single forming step, thus, speeding up fabrication of the ICE associated with the retrieved ICE design 305. After each of the multiple forming steps used to form the critical layer and the single forming step used to form the other (non-critical) layer, the computer system 305 instructs the measurement system 304 associated with the ICE fabrication system 300 to determine optical (e.g., complex refractive indices) and physical (e.g., thicknesses) characteristics of the formed sub-layers and layers. Moreover, prior to forming of at least some of the critical layers of the ICE, the computer system 305 instructs the ICE fabrication system 300 to adjust subsequent forming steps used to form one or more remaining layers specified by the retrieved ICE design 307, based on results of the determined characteristics of the formed sub-layers and layers.

(4.2) Fabrication of ICE Having Critical Layer(s)

Figure 4:
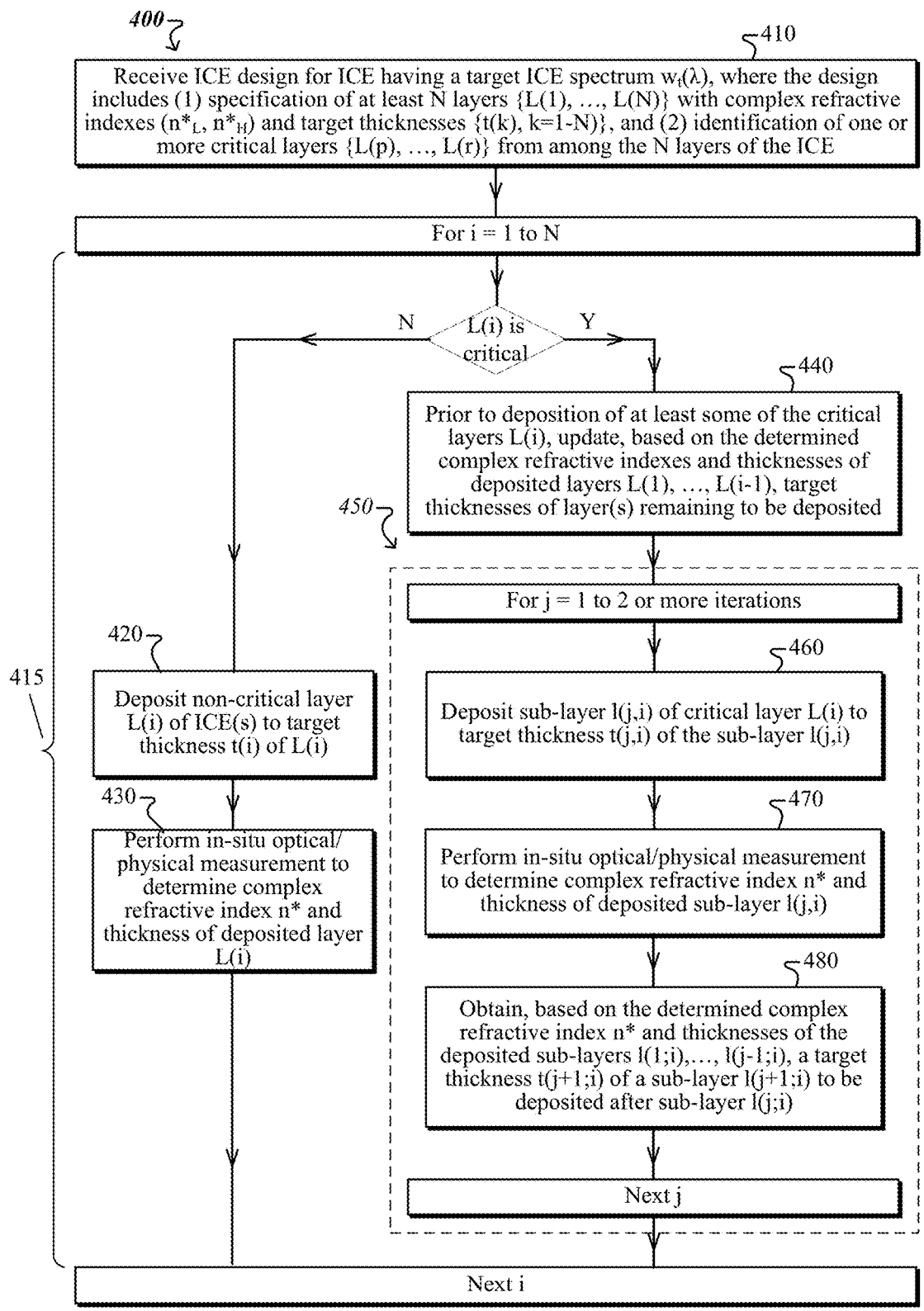
FIG. 4 is a flowchart showing an example of a process for selectively forming layers of an ICE associated with an ICE design that specifies critical and non-critical layers.

FIG. 4 is a flow chart of an example of an ICE fabrication process 400 for fabricating ICEs that have critical layer(s). Process 400 can be implemented in conjunction with ICE fabrication system 300 to fabricate one or more such ICEs. In such a context, the process 400 can be implemented as instructions encoded in the memory of the computer system 305, such that execution of the instructions, by the one or more hardware processors of the computer system 305, causes the ICE fabrication system 300 to perform the following operations.

At 410, an ICE design is received. The received ICE design includes specification of a substrate and N layers $L(1), L(2), \ldots, L(N)$, each having a different complex refractive index from its adjacent layers, and specification of target complex refractive indices and thicknesses $t_S, t(1), t(2), \ldots, t(N)$. In this manner, an ICE fabricated in accordance with the received ICE design selectively weights, when operated, light in at least a portion of a wavelength range by differing amounts. The differing amounts weighted over the wavelength range correspond to a target optical spectrum $w_t(\lambda)$ of the ICE and are related to a characteristic of a sample. For example, a design process for determining the specified (1) substrate and number N of layers of the ICE, each having a different complex refractive index from its adjacent layers, and (2) complex refractive indices and thicknesses of the substrate and the N layers that correspond to the target optical spectrum $w_t(\lambda)$ of the ICE is described above in connection with FIG. 2A. The received ICE design also includes identification of one or more critical layers from among the specified number of layers. A layer of the ICE is identified as a critical layer if potential variations of its thickness or complex refractive index due to expected variations of the fabrication process can cause degradation of the ICE's performance relative to a target performance that exceeds a threshold degradation. Otherwise, the layer is identified as a non-critical layer. For example, the target performance represents an accuracy with which the ICE is expected to predict known values of the characteristic corresponding to a set of validation spectra of the sample. Here, predicted values of the characteristic are obtained by integration of the validation spectra of the sample respectively weighted by the ICE. An analysis for identifying critical layers of an ICE design is described above in connection with FIG. 2B.

Loop 415 is used to fabricate one or more ICEs based on the received ICE design. Each iteration "i" of the loop 415 is used to form a layer L(i) of the N specified layers of the ICE based on whether the layer L(i) is identified by the received ICE design as a critical layer or as a non-critical layer.

If the layer L(i) is identified as a non-critical layer, the non-critical layer L(i) is formed using a single forming step, at 420. Here, the non-critical layer L(i) is formed to a target thickness t(i). The target thickness t(i) of the non-critical layer L(i) can be specified by the received ICE design or updated based on optimization(s) carried out before forming one or more of the critical layers of the ICE. In the example illustrated in FIG. 3, the deposition source 303 having a deposition rate R is used for a time duration $\Delta T(i)=t(i)/R$ to deposit the non-critical layer L(i) to its target thickness.

At 430, after the layer L(i) is formed, in-situ optical and/or physical measurements are performed to determine one or more characteristics of the formed layer L(i). In the example illustrated in FIG. 3, the in-situ optical measurements performed using the measurement system 304 include at least one of ellipsometry, spectroscopy and optical monitoring. In-situ physical measurements performed using the measurement system 304 include physical monitoring, e.g., with a crystal microbalance. Results of these in-situ optical and/or physical measurements are used to determine optical characteristics—e.g., complex refractive indices $n^{*}_H$ and $n^{*}_L$—and physical characteristics—e.g., thicknesses t'(1), t'(2), ..., t'(i−1), t'(i)—of the formed layers: the just-completed non-critical layer L(i) and the layers L(1), L(2), ..., L(i−1) formed in previous iterations of the loop 415. If necessary, a deposition rate used to form the other layers L(i+1), L(i+2), ..., L(N) remaining to be formed can be adjusted based on determined values of the complex refractive indices and thicknesses of the formed layers. Alternatively or additionally, complex refractive indices corresponding to the other layers L(i+1), L(i+2), ..., L(N) remaining to be formed can be further adjusted based on the determined values of the complex refractive indices and thicknesses of the formed layers.

Remaining non-critical layers of the ICE will be formed using the non-critical branch of the loop 415 that includes the sequence of the single forming step, at 420, followed by the measurement step, at 430.

If the layer L(i) is identified as a critical layer, it will be formed by first performing an update of the ICE design, at 440, followed by multiple forming steps in accordance with a sub-loop 450.

At 440, target thicknesses of layers L(i), L(i+1), ..., L(N) remaining to be formed are updated based on the determined complex refractive indices and thicknesses of the formed layers L(1), L(2), ..., L(i−1). This updating step is performed to compensate for performance degradation of the ICE relative to the target performance caused by deviations of the determined complex refractive indices and thicknesses of the formed layers from their respective complex refractive indices and the target thicknesses specified in the received ICE design. In some implementations, the updating step is performed prior to forming each of the one or more critical layers identified in the receive ICE design. However, as updating of the received ICE design is not necessary when the first layer L(1) to be formed is a critical layer, the updating step will be skipped prior to forming the first layer L(1) in this case. In some implementations, triggering of the updating step is conditional. Here, an SEC(i−1) is calculated for an ICE having the first layers L(1), L(2), ..., L(i−1) formed with the determined thicknesses t'(1), t'(2), ..., t'(i−1), and the other layers L(i), L(i+1), ..., L(N) remaining to be formed with target thicknesses t(i), t(i+1), ..., t(N). If the calculated SEC(i−1) is larger than a target $SEC_t$ by a value that exceeds a threshold value, the updating step is triggered, otherwise it is skipped. As described above, the target $SEC_t$ is specified, either explicitly or implicitly, by the received ICE design.

The updating step constrains the total number of layers of the ICE to N and the thicknesses of the first layers L(1), L(2), ..., L(i−1) (which have been already formed) to the determined thicknesses t'(1), t'(2), ..., t'(i−1). In this manner, the optimization process obtains, in analogy with the process 200 described above in connection with FIG. 2A, updated target thicknesses t"(i), t"(i+1), ..., t"(N) of the other layers L(i), L(i+1), ..., L(N) remaining to be formed, such that an updated target SECt" is minimum for an ICE having the first layers L(1), L(2), ..., L(i−1) formed with the determined thicknesses t'(1), t'(2), ..., t'(i−1), and the other layers L(i), L(i+1), ..., L(N) remaining to be formed with the updated target thicknesses t"(i), t"(i+1), ..., t"(N).

The sub-loop 450 includes two or more iterations "j", each of the iterations used to form, at 460, a sub-layer l(j;i) of the critical layer L(i). Here, the sub-layer l(j;i) is formed to a sub-layer target thickness t(j;i). The sub-layer target thickness t(j;i) of the sub-layer l(j;i) is specified based on the updated target thickness t(i) of the critical layer L(i) and various rules. Examples of such rules for specifying the target thicknesses of the multiple sub-layers of each of the critical layers are described below in connection with FIGS. 5A and 6A. As illustrated in FIG. 3, the deposition source 303 having a deposition rate R is used for a time duration $\Delta T(j;i)=t(j;i)/R$ to deposit the sub-layer l(j;i) of the critical layer L(i) to its sub-layer target thickness t(j;i).

At 470, after the sub-layer l(j;i) of the critical layer L(i) is formed, in-situ optical and/or physical measurements are performed to determine one or more characteristics of the formed sub-layer l(j;i). In the example illustrated in FIG. 3, the in-situ optical measurements performed using the measurement system 304 include at least one of ellipsometry, spectroscopy and optical monitoring. In-situ physical measurements performed using the measurement system 304 include physical monitoring, e.g., with a crystal microbalance. Results of these in-situ optical and/or physical measurements are used to determine (1) a complex refractive index $n^{*}_H$ or $n^{*}_L$ and sub-layer thicknesses t'(1;i), t'(2;i), ..., t'(j−1;i), t'(j;i) of the sub-layers l(1;i), l(2;i), ..., l(j−1;i) formed in previous iterations of the sub-loop 450 and the just-completed sub-layer l(j;i), and (2) complex refractive indices $n^{*}_H$ and $n^{*}_L$ and thicknesses t'(1), t'(2), ..., t'(i−1) of the layers L(1), L(2), ..., L(i−1) formed in previous iterations of the loop 415.

If necessary, a deposition rate used to form remaining sub-layers of the critical layer L(i) currently being formed and the other layers L(i+1), L(i+2), ..., L(N) remaining to be formed can be adjusted based on determined values of the complex refractive indices and thicknesses of the formed sub-layers and layers. Alternatively or additionally, a complex refractive index of remaining sub-layers of the critical layer L(i) currently being formed and complex refractive indices corresponding to the other layers L(i+1), L(i+2), ..., L(N) remaining to be formed can be further adjusted based on the determined values of the complex refractive indices and thicknesses of the formed sub-layers and layers.

At 480, a sub-layer target thickness of a sub-layer to be formed next is obtained. In some implementations described in detail below in connection with FIG. 5A, a sub-layer target thickness t(j+1;i) of a sub-layer l(j+1;i) to be formed after completion of the current sub-layer l(j;i) is obtained based on (1) the updated target thickness t(i) of the critical layer L(i) obtained at 440, and (2) various rules to account for the determined complex refractive index $n^{*}_H$ or $n^{*}_L$ and thicknesses of the formed sub-layers l(1;i), l(2;i), . . . , l(j;i). In some implementations described in detail below in connection with FIG. 6A, the foregoing techniques for obtaining the sub-layer target thickness t(j+1;i) of the next sub-layer l(j+1;i) is applied only after having formed a particular number of sub-layers. In such case, the particular number of sub-layers were formed to predetermined sub-layer target thicknesses.

In this manner, remaining sub-layers of the critical layer L(i) will be formed using respective iterations of the sub-loop 450. Moreover, remaining critical layers of the ICE will be formed using the critical branch of loop 415 that includes the sequence of updating the ICE design, at 440, followed by forming, in accordance with the multiple iterations of the sub-loop 450, two or more sub-layers for each of the remaining critical layers.

By implementing the process 400, fabrication of one or more ICEs can be faster and require less computational resources than conventional ICE fab processes. The reason for this benefit is that the conventional ICE fab processes update the ICE design before forming each of the N layers of the ICE, while the process 400 skips the updating step before forming the non-critical layers of the ICE, and updates the ICE design only before forming each of the critical layers of the ICE. As such, the cost of fabricating the one or more ICEs using the process 400 is lower than the cost of fabricating ICEs using conventional ICE fabrication processes. In this manner, low cost logging tool(s) like the logging tool(s) 110—described above in connection with FIGS. 1A-1C—can be provided.

Multiple examples of forming a critical layer of an ICE design using multiple forming steps to form respective sub-layers of the critical layer are described below. The various implementations are based on different rules for establishing target thicknesses of the sub-layers.

(4.3) Techniques for Fabricating Critical Layer of ICE

Figure 5A:
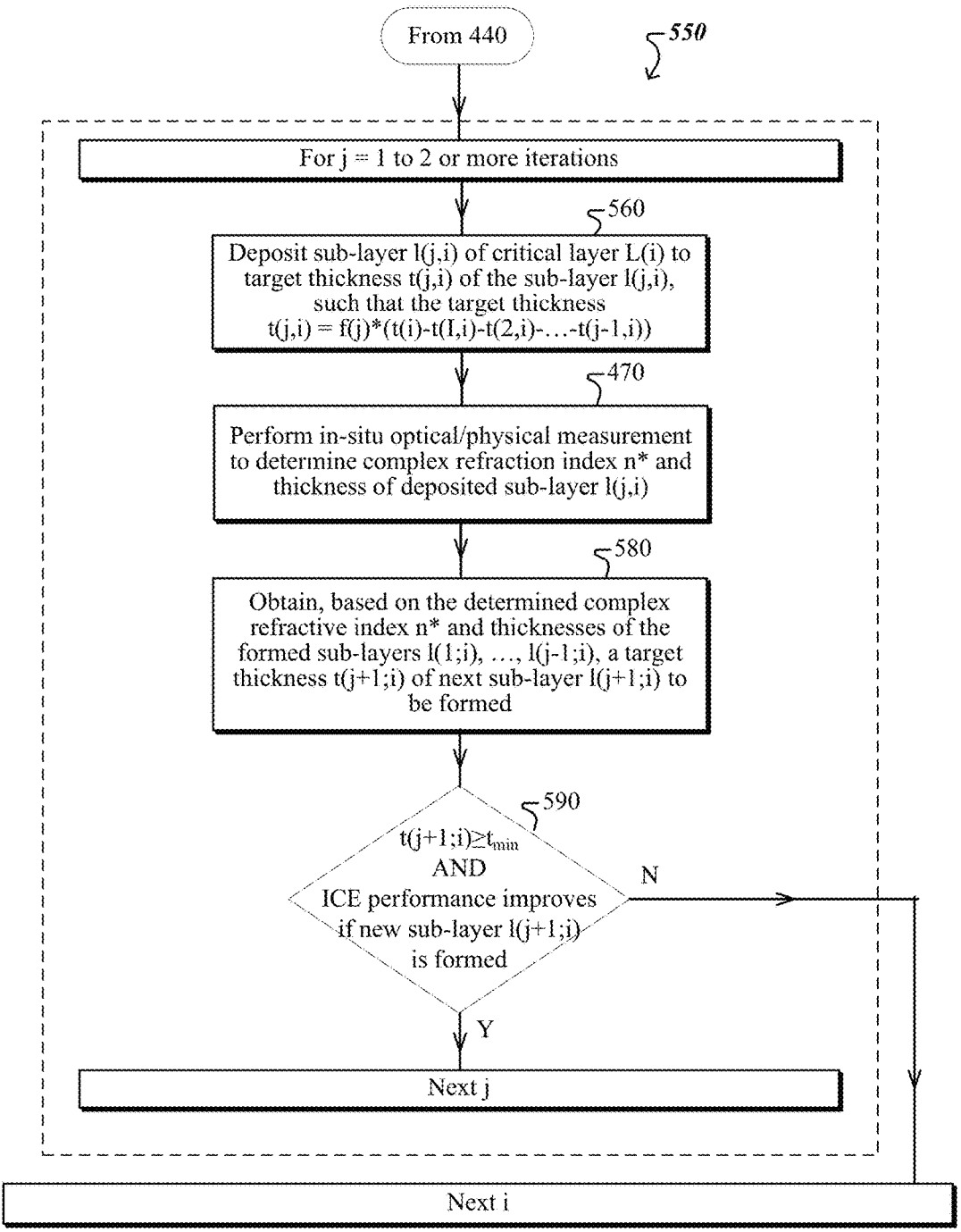
FIG. 5A is a flowchart showing an example of a process for forming critical layers of an ICE.

FIG. 5A is a flow chart of an example of a process 550 for forming a critical layer of an ICE design. The process 550 can be implemented as the sub-loop 450 of the ICE fab process 400 to form the critical layers of one or more ICEs. In this manner, the process 550 in conjunction with the process 400 can be performed using the ICE fabrication system 300 to fabricate one or more ICEs. In such a context, the process 550 can be implemented as instructions encoded in the memory of the computer system 305, such that execution of the instructions, by the one or more hardware processors of the computer system 305, causes the ICE fabrication system 300 to perform the following operations.

When the process 550 is implemented as the sub-loop 450 of the process 400, input of the process 550 includes an indication that the layer L(i), to be formed by the $i^{th}$ iteration of the loop 415, is a critical layer. Also included in the input of the process 550 are the determined complex refractive indices $n^{*}_H$ and $n^{*}_L$ and thicknesses t'(1), t'(2), . . . , t'(i−1) of the layers L(1), L(2), . . . , L(i−1) of the ICE formed in previous iterations of the loop 415. Further included in the input of the process 550 are the updated target thicknesses t(i), t(i+1), . . . , t(N) of the other layers L(i), L(i+1), . . . , L(N) of the ICE remaining to be formed.

The process 550 includes two or more iterations "j", each of the iterations being used to form, at 560, a sub-layer l(j;i) of the critical layer L(i). Here, the sub-layer l(j;i) of the critical layer L(i) is formed to a sub-layer target thickness t(j;i) equal to a fraction of the remaining thickness of the critical layer L(i). As such, $$t(j;i) = f(j) \cdot [t(i) - t'(1;i) - t'(2;i) - \ldots - t'(j-1;i)], \quad (1)$$

where t(i) is the target thickness of the critical layer L(i), and t'(1;i), t'(2;i), . . . , t'(j−1;i) are determined thicknesses of the sub-layers l(1;i), l(2;i), . . . , l(j−1;i) of the critical layer L(i) formed in previous iterations of the process 550. The fraction 0<f(j)<1 can be the same for all iterations of the process 550, or can have different values for different iterations.

For example, the fraction of the remaining thickness of the critical layer is 50%. In this case, during the first iteration of the process 550, a first sub-layer l(1;i) is formed to a first sub-layer target thickness of t(1;i)=0.5t(i); during the second iteration of the process 550, a second sub-layer l(2;i) is formed to a second sub-layer target thickness of t(2;i)=0.25t(i), such that the cumulative thickness of the two formed sub-layers is about 0.75t(i); during the third iteration of the process 550, a third sub-layer l(3;i) is formed to a third sub-layer target thickness of t(3;i)=0.125t(i), such that the cumulative thickness of the three formed sub-layers is about 0.875t(i); and so on. Such an example of deposition of a critical layer is described in detail below in connection with FIG. 5B. As another example, the fraction of the remaining thickness of the critical layer is 90%. In this case, during the first iteration of the process 550, a first sub-layer l(1;i) is formed to a first sub-layer target thickness of t(1;i)=0.9t(i); during the second iteration of the process 550, a second sub-layer l(2;i) is formed to a second sub-layer target thickness of t(2;i)=0.09t(i), such that the cumulative thickness of the two formed sub-layers is about 0.99t(i); and so on.

As yet another example, a first fraction (e.g., 80% or 90%) is used for the sub-layer target thickness of the first few predetermined sub-layers (e.g., for the first sub-layer) of the total sub-layers, and a second fraction (e.g., 50%) is used for the sub-layer target thickness of the remaining sub-layers of the total sub-layers. Generally, the first deposited sub-layer is a larger fraction of the total layer thickness than subsequent sub-layers. Examples of such depositions of a critical layer based on two or more fractions are described in detail below in connection with FIGS. 6B-6C.

A deposition source having a deposition rate R is used, at 560, for a time duration ΔT(j;i)=t(j;i)/R to deposit the sub-layer l(j;i) of the critical layer L(i) to its sub-layer target thickness t(j;i).

At 470, after the sub-layer l(j;i) of the critical layer L(i) is formed, in-situ optical and/or physical measurements are performed to determine one or more characteristics of the formed sub-layer l(j;i). This step is described in detail above in connection with FIG. 4.

At 580, a sub-layer target thickness t(j+1;i) of a sub-layer l(j+1;i) to be formed next is obtained. Here, the sub-layer target thickness t(j+1;i) of a sub-layer l(j+1;i) to be formed next is obtained using Equation (1) based on the updated target thickness t(i) of the critical layer L(i)—obtained from the received ICE design or from the ICE design updated at 440—and the determined thicknesses of the formed sub-layers l(1;i), l(2;i), . . . , l(j;i).

At 590, a determination is made whether forming the new sub-layer l(j+1;i) of the critical layer L(i) is feasible, and if so, whether performance of an ICE with a critical layer L(i) that contains the formed j sub-layers would improve if the new sub-layer l(j+1;i) of the critical layer L(i) were formed. For the first few iterations of the process 550, when the cumulative determined thickness of the formed sub-layers l(1;i), l(2;i), . . . , l(j;i) may still be far from the target thickness t(i) of the critical layer L(i), adding a new sub-layer l(j+1;i) to the critical layer L(i) should improve the ICE performance. By performing additional iterations of the process 550 to form respective additional sub-layers of the critical layer L(i), the determined cumulative thickness of the formed sub-layers l(1;i), l(2;i), . . . , l(j;i) approaches asymptotically the target thickness t(i) of the critical layer L(i). A such, after a particular number of iterations $j_p$ during which respective sub-layers l(1;i), l(2;i), . . . , l($j_p$;i) of the critical layer L(i) were formed, forming an additional sub-layer l($j_p$+1;i) may not improve performance of the ICE having a critical layer L(i) with $j_p$ formed sub-layers.

However, even if performance of the ICE having a critical layer L(i) with $j_p$ formed sub-layers would improve when forming an additional sub-layer l($j_p$+1;i), in case a sub-layer target thickness t($j_p$+1;i) of the latter is smaller than a lower bound t($j_p$+1;i)<$t_{min}$ (allowed by capability 308 of the ICE fabrication system 300), then such an additional sub-layer l($j_p$+1;i) could not be accurately formed by the ICE fabrication system 300. Hence, in case the sub-layer thickness t($j_p$+1;i) obtained at 580 is less than $t_{min}$, the forming of the critical layer L(i) is completed.

Else, if the established sub-layer thickness t($j_p$+1;i) is larger than or equal to $t_{min}$, an SEC(j) is calculated for an ICE having (A) formed layers L(1), L(2), . . . , L(i−1) with the determined thicknesses t'(1), t'(2), . . . , t'(i−1), (B) formed sub-layers l(1;i), l(2;i), . . . , l(j;i) of the critical layer L(i) with the determined sub-layer thicknesses t'(1;i), t'(2;i), . . . , t'(j;i), and (C) the other layers L(i+1), L(i+2), . . . , L(N) remaining to be formed with target thicknesses t(i+1), t(i+2), . . . , t(N). Also, another SEC(j+1) is calculated for an ICE having (A) formed layers L(1), L(2), . . . , L(i−1) with the determined thicknesses t'(1), t'(2), . . . , t'(i−1), (B) formed sub-layers l(1;i), l(2;i), . . . , l(j;i) of the critical layer L(i) with the determined sub-layer thicknesses t'(1;i), t'(2;i), . . . , t'(j;i), (C) the other layers L(i+1), L(i+2), . . . , L(N) remaining to be formed with target thicknesses t(i+1), t(i+2), . . . , t(N), and (D) one additional sub-layer l(j+1;i) of the critical layer L(i) to be formed to a target thickness t(j+1;i) obtained at 580.

If the SEC(j+1) is larger than or equal to the SEC(j), then addition of another sub-layer l(j+1;i) would degrade or merely maintain performance of the ICE having the critical layer L(i) with j sub-layers. Hence, the forming of the critical layer L(i) is completed. Else, if the SEC(j+1) is less than the SEC(j), then addition of another sub-layer l(j+1;i) would improve performance of the ICE having the critical layer L(i) with j sub-layers. Hence, the forming of the critical layer L(i) based on the process 550 will continue with a new forming step 560 to form the additional sub-layer l(j+1;i) of the critical layer L(i) to the sub-layer target t(j+1,i).

In this manner, remaining sub-layers of the critical layer L(i) will be formed using respective iterations of the process 550.

Example 1

Figure 5B:
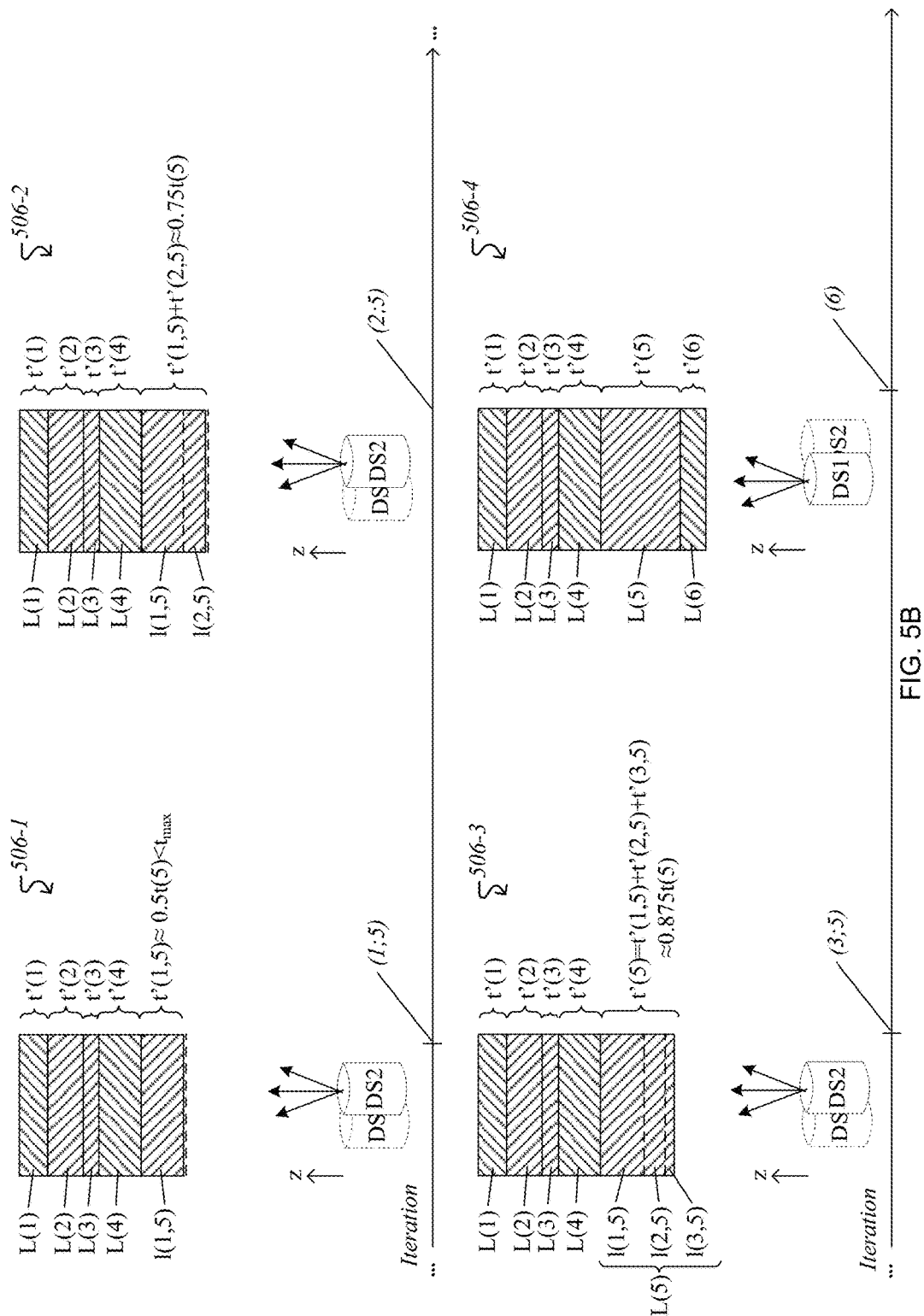
FIG. 5B shows aspects of the process for forming a critical layer of an ICE.

FIG. 5B shows aspects of forming a critical layer L(5) of the ICE design 245 described above in connection with FIGS. 2A-2B. In this example, the process 550 is used to form the critical layer L(5). Prior to forming the critical layer L(5), layers L(1), L(2), L(3) and L(4) were formed in accordance with the process 400, and their thicknesses were determined to be t'(1), t'(2), t'(3) and t'(4), respectively. Additionally, target thicknesses t(5), t(6), t(7) and t(8) of the layers remaining to be formed have been updated based on the determined thicknesses of the formed layers, in accordance with step 440 of the process 400.

Prior to the first iteration (1;5) of the forming of the critical layer L(5), a first sub-layer target thickness t(1;5)=0.5t(5) is obtained in accordance with Equation (1), based on the target thickness of the critical layer t(5) and a fraction f(1)=0.5. As the obtained sub-layer target thickness t(1;5) is smaller than a maximum allowed deposition thickness, t(1;5)<$t_{max}$, a first sub-layer l(1;5) is deposited, by the fabrication system 300, to the first sub-layer target thickness t(1;5) using a single deposition step. At the end of the first iteration (1;5), an instance 506-1 of the ICE includes the deposited layers L(1), L(2), L(3), L(4) and a first deposited sub-layer l(1;5) of the critical layer L(5). The thickness of the deposited first sub-layer l(1;5) is determined, by the measurement system 304 associated with the fabrication system 300, to be t'(1,5). At this time, a second sub-layer target thickness t(2;5)=0.5[t(5)−t'(1,5)]≈0.25t(5) for sub-layer l(2;5) to be deposited next is obtained in accordance with Equation (1), based on the target thickness of the critical layer t(5), the determined thickness t'(1;5) of the first deposited sub-layer, and a fraction f(2)=0.5. Moreover, here it is verified that (1) the obtained second sub-layer target thickness t(2;5) is larger than a minimum allowed deposition thickness, t(2;5)>$t_{min}$, and (2) adding a second sub-layer l(2;5) to the instance 506-1 of the ICE would improve its performance.

In view of the foregoing verification, a second iteration (2;5) of the forming of the critical layer L(5) is performed. The second sub-layer l(2;5) is deposited, by the fabrication system 300, to the obtained second sub-layer target thickness t(2;5) using a single deposition step. At the end of the second iteration (2;5), an instance 506-2 of the ICE includes the deposited layers L(1), L(2), L(3), L(4) and first two deposited sub-layers l(1;5), l(2;5) of the critical layer L(5). The thickness of the deposited second sub-layer l(2;5) is determined, by the measurement system 304 associated with the fabrication system 300, to be t'(2,5). Hence, a cumulative thickness of the first two deposited sub-layers l(1;5), l(2;5) of the critical layer L(5) is t'(1;5)+t'(2;5)≈0.75t(5). At this time, a third sub-layer target thickness t(3;5)=0.5[t(5)−t'(1, 5)−t'(2,5)]≈0.125t(5) for sub-layer l(3;5) to be deposited next is obtained in accordance with Equation (1), based on the target thickness of the critical layer t(5), the determined thicknesses t'(1;5), t'(2;5) of the first two deposited sub-layers, and a fraction f(3)=0.5. Moreover, here it is verified that (1) the obtained third sub-layer target thickness t(3;5) is larger than or equal to the minimum allowed deposition thickness, t(3;5)≥$t_{min}$, and (2) adding a third sub-layer l(3;5) to the instance 506-2 of the ICE would improve its performance.

In view of the foregoing verification, a third iteration (3;5) of the forming of the critical layer L(5) is performed. The third sub-layer l(3;5) is deposited, by the fabrication system 300, to the obtained third sub-layer target thickness t(3;5) using a single deposition step. At the end of the third iteration (3;5), an instance 506-3 of the ICE includes the deposited layers L(1), L(2), L(3), L(4) and first three deposited sub-layers l(1;5), l(2;5), l(3;5) of the critical layer L(5). The thickness of the deposited third sub-layer l(3;5) is determined, by the measurement system 304 associated with the fabrication system 300, to be t'(3;5). Hence, a cumulative thickness of the first three deposited sub-layers layers l(1;5), l(2;5), l(3;5) of the critical layer L(5) is t'(1;5)+t'(2;5)+t'(3; 5)≈0.875t(5). At this time, a fourth sub-layer target thickness t(4;5)=0.5[t(5)–t'(1,5)–t'(2,5)–t'(3,5)]≈0.0625t(5) for sub-layer l(4;5) to be deposited next is obtained in accordance with Equation (1), based on the target thickness of the critical layer t(5), the determined thicknesses t'(1;5), t'(2;5), t'(3;5) of the first three deposited sub-layers, and a fraction f(4)=0.5. Here, it is found that either (1) the obtained fourth sub-layer target thickness t(4;5) is smaller than the minimum allowed deposition thickness, t(4;5)<$t_{min}$, or (2) adding a fourth sub-layer l(4;5) to the instance 506-3 of the ICE would degrade its performance. In view of the foregoing finding, the forming of the critical layer L(5) is completed.

In this example, the next layer L(6) to be formed is a non-critical layer. Hence, the non-critical layer L(6) is deposited, by the fabrication system 300 in accordance with the process 400, to a target thickness t(6) using a single deposition step. At the end of the current iteration (6), an instance 506-4 of the ICE includes the deposited layers L(1), L(2), L(3), L(4), L(5) and L(6). The thickness of the deposited sixth layer L(6) is determined, by the measurement system 304 associated with the fabrication system 300, to be t'(6).

Another example of forming a critical layer of an ICE design using multiple forming steps to form respective sub-layers of the critical layer is described below.

(4.4) Other Techniques for Fabricating Critical Layer of ICE

Figure 6A:
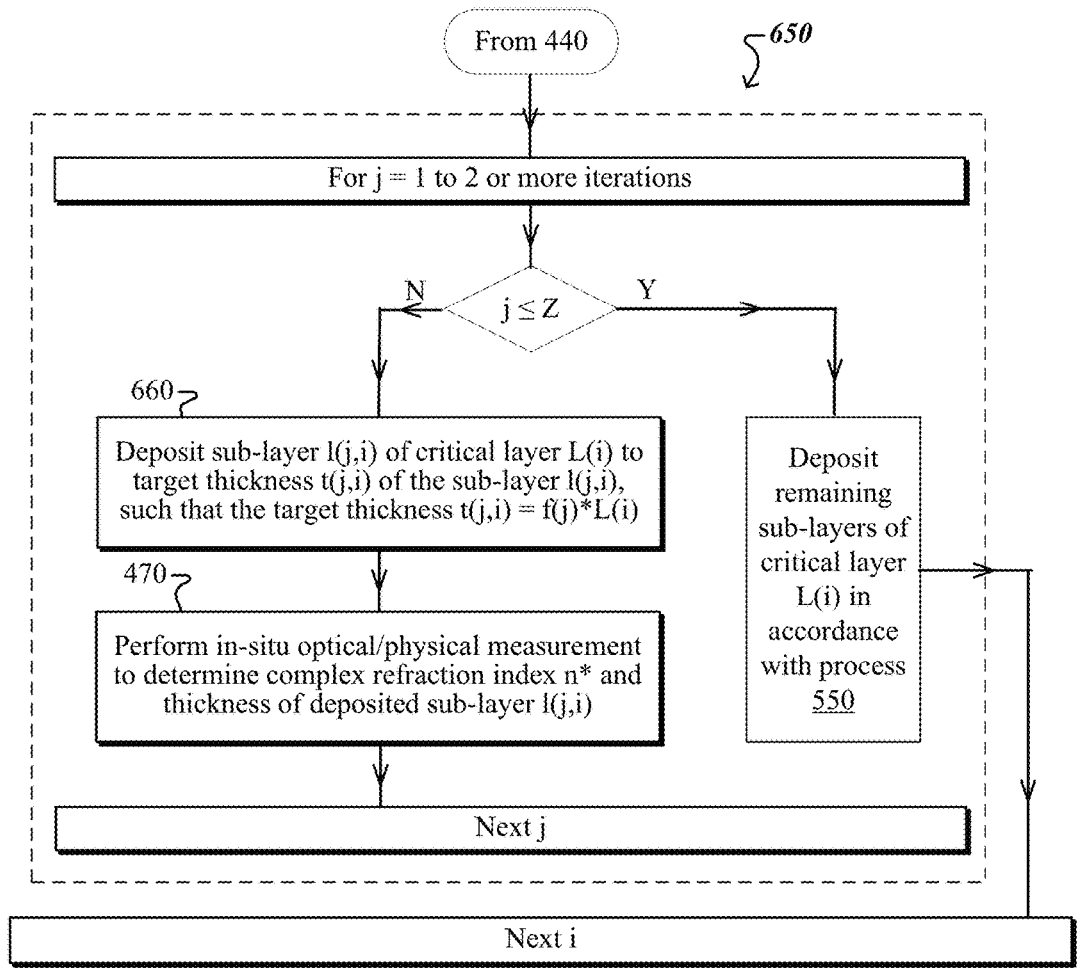
FIG. 6A is a flowchart showing another example of a process for forming critical layers of an ICE.

FIG. 6A is a flow chart of an example of a process 650 for forming a critical layer of an ICE design. The process 650 can be implemented as the sub-loop 450 of the ICE fab process 400 to form the critical layers of one or more ICEs. In this manner, the process 650 in conjunction with the process 400 can be performed using the ICE fabrication system 300 to fabricate one or more ICEs. In such a context, the process 650 can be implemented as instructions encoded in the memory of the computer system 305, such that execution of the instructions, by the one or more hardware processors of the computer system 305, causes the ICE fabrication system 300 to perform the following operations.

When the process 650 is implemented as the sub-loop 450 of the process 400, input of the process 650 includes an indication that the layer L(i), to be formed by the $i^{th}$ iteration of the loop 415, is a critical layer. Also included in the input of the process 650 are the determined complex refractive indices $n'_H$ and $n'_L$ and thicknesses t'(1), t'(2), ..., t'(i–1) of the layers L(1), L(2), ..., L(i–1) of the ICE formed in previous iterations of the loop 415. Further included in the input of the process 650 are the updated target thicknesses t(i), t(i+1), ..., t(N) of the other layers L(i), L(i+1), ..., L(N) of the ICE remaining to be formed.

The process 650 includes two or more iterations "j", each of the first Z iterations is used to form, at 660, a sub-layer l(j;i) of the critical layer L(i) based on a predetermined sub-layer target thickness. Here, each of the first Z sub-layers of the critical layer L(i) is formed to a sub-layer target thickness t(j;i) equal to a fraction of the target thickness of the critical layer L(i). As such, $$t(j;i)=f(j)\cdot t(i), \text{ for } j=1,\ldots,Z, \tag{2}$$

where t(i) is the target thickness of the critical layer L(i), and the fraction 0<f(j)<1 can be the same for all of the Z iterations of the process 550, or can have different values for different iterations. Moreover the fraction is chosen such that a sub-layer target thickness t(j;i) does not exceed a maximum allowed deposition thickness, t(j;i)<$t_{max}$.

For example, if Z=2 and f(1)=f(2)=½, then the first two sub-layers l(1;i), l(2;i) of the critical layer L(i) are formed to sub-layer target thickness t(1;i)=t(2;i)=t(i)/3<$t_{max}$. As another example, when Z=3, f(1)=½, f(2)=⅓ and f(3)=¼, then the first sub-layer l(1;i) is formed to a first sub-layer target thickness t(1;j)=t(i)/2<$t_{max}$, the second sub-layer l(2;i) is formed to a second sub-layer target thickness t(2;j)=t(i)/3, and the third sub-layer l(3;i) is formed to a third sub-layer target thickness t(3;j)=t(i)/4.

A deposition source having a deposition rate R is used, at 660, for a time duration ΔT(j;i)=t(j;i)/R to deposit the sub-layer l(j;i) of the critical layer L(i) to its sub-layer target thickness t(j;i).

At 470, after the sub-layer l(j;i) of the critical layer L(i) is formed, in-situ optical and/or physical measurements are performed to determine one or more characteristics of the formed sub-layer l(j;i). This step is described in detail above in connection with FIG. 4.

In this manner, remaining sub-layers of the first Z sub-layers of the critical layer L(i) will be formed using the sequence of operations 660 and 470.

A next sub-layer t(Z+1;i) of the critical layer L(i) will be formed to a sub-layer target thickness t(Z+1;i) equal a to remainder of the target thickness of the critical layer L(i). As such, $$t(Z+1;i)=t(i)-t'(1;i)-t'(2;i)-\ldots-t'(Z;i), \tag{3}$$

where t(i) is the target thickness of the critical layer L(i), and t'(1;i), t'(2;i), ..., t'(Z;i) are determined thicknesses of the sub-layers l(1;i), l(2;i), ..., l(Z;i) of the critical layer L(i) formed in first Z iterations of the process 650.

The process 550—described above in connection with FIG. 5A—is used here to form the next sub-layer l(Z+1;i) to the sub-layer target thickness t(Z+1;i) obtained using Equation (3). Accordingly, two or more iterations of the process 550 are used to form respective sub-sub-layers l(n|Z+1;i) of the sub-layer l(Z+1;i) to sequentially smaller target thicknesses obtained in accordance with the following modification of Equation (1):

$$t(n|Z+1;i)=f(n)\cdot[t(Z+1;i)-t'(1|Z+1;i)-t'(2|Z+1;i)-\ldots-t'(n-1|Z+1;i)]. \tag{1'}$$

Here, the t(Z+1;i) is the sub-layer target thickness of the sub-layer l(Z+1;i) obtained using Equation (3), and t'(1|Z+1;i), t'(2|Z+1;i), ..., t'(n-1|Z+1;i) are determined thicknesses of the sub-sub-layers l(1|Z+1;i), l(2|Z+1;i), ..., l(n-1|Z+1;i) of the sub-layer l(Z+1;i) formed in previous iterations of the process 550. In this manner, the cumulative thickness of the formed sub-sub-layers l(1|Z+1;i), ..., l(n|Z+1;i) of the sub-layer l(Z+1;i) approaches asymptotically the sub-layer target thickness of the sub-layer l(Z+1;i). As described above in connection with FIG. 5A, the forming of the sub-layer l(Z+1;i)—and thus the forming of the critical layer L(i)—is completed when either (1) a sub-sub-layer target thickness t(n+1|Z+1;i) of an additional sub-sub-layer l(n+1|Z+1;i) is smaller than the minimum allowed deposition thickness, t(n+1|Z+1;i)<$t_{min}$, or (2) forming an additional sub-sub-layer l(n+1|Z+1;i) would degrade or merely maintain performance of the ICE having a critical layer L(i) that includes formed sub-layers l(1;i), ..., l(Z;i) and a sub-layer l(Z+1;i) with formed sub-sub-layers l(1|Z+1;i), ..., l(n|Z+1;i).

A critical layer L(i) can be formed faster using the process 650 than using the process 550 because a sub-layer target thickness is predetermined for the first Z iterations of the process 650, while the sub-layer target thickness is determined for each iteration of the process 550. Additionally, skipping the determining of the sub-layer target thicknesses for the first Z iterations of the process 650 can potentially decrease computational resources required by the process 650 relative to the process 550. At least for these reasons, forming critical layers of an ICE design based on the process 650 may be more cost effective than forming the critical layers based on the process 550.

Examples of forming a critical layer of an ICE design using multiple forming steps to form respective sub-layers of the critical layer in accordance with the process 650 is described below.

Example 2

Figure 6B:
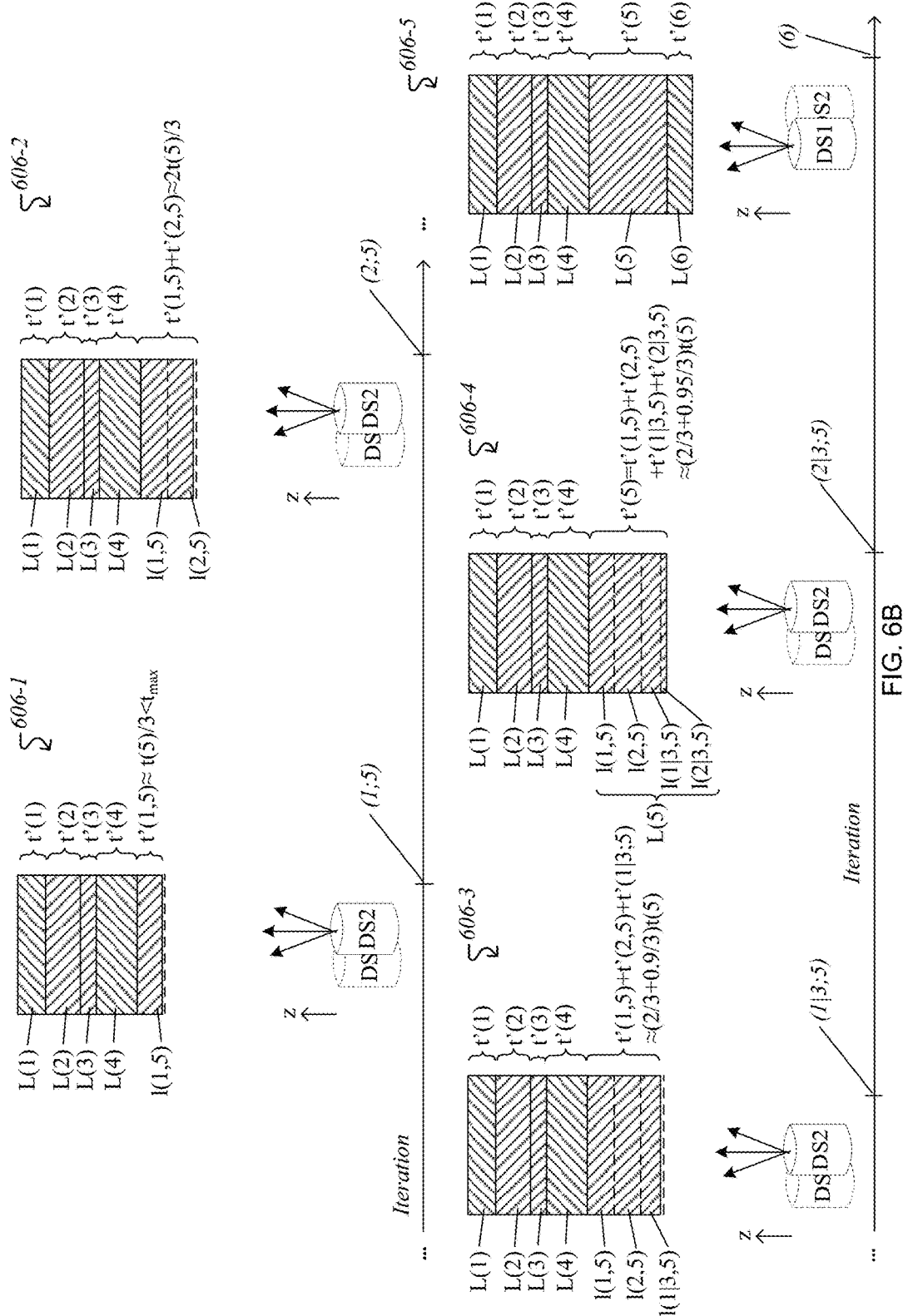
FIGS. 6B-6C show aspects of the other process for forming a critical layer of an ICE.

FIG. 6B shows other aspects of forming a critical layer L(5) of the ICE design 245 described above in connection with FIGS. 2A-2B. In this example, the process 650 is used to form the critical layer L(5). Prior to forming the critical layer L(5), layers L(1), L(2), L(3) and L(4) were formed in accordance with the process 400, and their thicknesses were determined to be t'(1), t'(2), t'(3) and t'(4), respectively. Additionally, target thicknesses t(5), t(6), t(7) and t(8) of the layers remaining to be formed have been updated based on the determined thicknesses of the formed layers, in accordance with step 440 of the process 400. In this example, the first two sub-layers of the critical layer L(5) will be formed using a predetermined sub-layer target thickness t(1;5)=t(2;5)=t(5)/3. The latter is obtained by substituting in Equation (2) the target thickness of the critical layer t(5), Z=2 and a fraction f(1)=f(2)=⅓.

A first iteration (1;5) of the forming of the critical layer L(5) is performed to form the first sub-layer l(1;5) to the predetermined sub-layer target thickness t(1;5)=t(5)/3. As the predetermined sub-layer target thickness t(1;5) is smaller than a maximum allowed deposition thickness, t(1;5)<$t_{max}$, the first sub-layer l(1;5) is deposited, by the fabrication system 300, to the first sub-layer target thickness t(1;5) using a single deposition step. At the end of the first iteration (1;5), an instance 606-1 of the ICE includes the deposited layers L(1), L(2), L(3), L(4) and a first deposited sub-layer l(1;5) of the critical layer L(5). The thickness of the deposited first sub-layer l(1;5) is determined to be t'(1,5) by the measurement system 304 associated with the fabrication system 300.

A second iteration (2;5) of the forming of the critical layer L(5) is performed to form the second and last sub-layer l(2;5) to the predetermined sub-layer target thickness t(2;5)=t(5)/3 using a single deposition step. At the end of the second iteration (2;5), an instance 606-2 of the ICE includes the deposited layers L(1), L(2), L(3), L(4) and first two deposited sub-layers l(1;5), l(2;5) of the critical layer L(5). The thickness of the deposited second sub-layer l(2;5) is determined, by the measurement system 304 associated with the fabrication system 300, to be t'(2,5). Hence, a cumulative thickness of the first two deposited sub-layers l(1;5), l(2;5) of the critical layer L(5) is t'(1;5)+t'(2;5) 2t(5)/3.

The process 550—described above in connection with FIG. 5A—is used next to form a $3^{rd}$ sub-layer l(3;5) of the critical layer L(5) to a $3^{rd}$ sub-layer target thickness t(3;5). The latter is obtained—in accordance with the Equation (3) based on the target thickness t(5) of the critical layer L(5) and the determined thicknesses t'(1;5), t'(2;5) of the first two deposited sub-layers—to be t(3;5)=t(5)-t'(1;5)-t'(2;5). In this manner, the $3^{rd}$ sub-layer l(3;5) will be formed using two or more forming steps to form respective sub-sub-layers l(n|3;5) thereof, where n=1, 2, . . . .

Prior to a $1^{st}$ iteration (1|3;5) of the forming of the $3^{rd}$ sub-layer l(3;5), a $1^{st}$ target thickness t(1|3;5)=0.9t(3;5) of a $1^{st}$ sub-sub-layer l(1|3;5) is obtained in accordance with Equation (1'), based on the $3^{rd}$ sub-layer target thickness t(3;5) of the $3^{rd}$ sub-layer l(3;5) and a fraction f(1)=0.9. The $1^{st}$ sub-sub-layer l(1|3;5) of the $3^{rd}$ sub-layer l(3;5) is deposited, by the fabrication system 300, to the $1^{st}$ target thickness t(1|3;5) using a single deposition step. At the end of this iteration (1|3;5), an instance 606-3 of the ICE includes the deposited layers L(1), L(2), L(3), L(4) and a $1^{st}$ deposited sub-sub-layer l(1|3;5) of the $3^{rd}$ sub-layer l(3;5) of the critical layer L(5). The thickness of the $1^{st}$ deposited sub-sub-layer l(1|3;5) is determined, by the measurement system 304 associated with the fabrication system 300, to be t'(1|3;5). At this time, a $2^{nd}$ target thickness t(2|3;5)=0.5[t(3;5)-t'(1|3;5)]≈0.05t(5)/3 for the $2^{nd}$ sub-sub-layer l(2|3;5) to be deposited next is obtained in accordance with Equation (1'), based on the target thickness of the $3^{rd}$ critical sub-layer t(3;5), the determined thickness t'(1|3;5) of the $1^{st}$ deposited sub-sub-layer l(1|3;5), and a fraction f(2)=0.5. Moreover, here it is verified that (1) the obtained $2^{nd}$ target thickness t(2|3;5) is larger than a minimum allowed deposition thickness, t(2|3;5)>$t_{min}$, and (2) adding a $2^{nd}$ sub-sub-layer l(2|3;5) to the instance 606-3 of the ICE would improve its performance.

In view of the foregoing verification, a $2^{nd}$ iteration (2|3;5) of the forming of the $3^{rd}$ sub-layer l(3;5) is performed. The $2^{nd}$ sub-sub-layer l(2|3;5) is deposited, by the fabrication system 300, to the obtained $2^{nd}$ target thickness t(2|3;5) using a single deposition step. At the end of this iteration (2|3;5), an instance 606-4 of the ICE includes the deposited layers L(1), L(2), L(3), L(4) and first two deposited sub-sub-layers l(1|3;5), l(2|3;5) of the $3^{rd}$ sub-layer l(3;5) of the critical layer L(5). The thickness of the deposited $2^{nd}$ sub-sub-layer l(2|3;5) is determined, by the measurement system 304 associated with the fabrication system 300, to be t'(2|3,5). Hence, a cumulative thickness of the first two deposited sub-sub-layers layers l(1|3;5), l(2|3;5) of the $3^{rd}$ sub-layer l(3;5) of the critical layer L(5) is t'(1|3;5)+t'(2|3;5)≈0.95t(5)/3. At this time, a $3^{rd}$ target thickness t(3|3;5)=0.5[t(5)-t'(1|3,5)-t'(2|3,5)]≈0.025t(5)/3 for the $3^{rd}$ sub-sub-layer l(3|3;5) to be deposited next is obtained in accordance with Equation (1'), based on the target thickness of the $3^{rd}$ critical sub-layer t(3;5), the determined thickness t'(1|3;5), t'(2|3;5) of the first two deposited sub-sub-layers l(1|3;5), l(2|3;5), and a fraction f(3)=0.5. Here, it is found that either (1) the obtained $3^{rd}$ target thickness t(3|3;5) is smaller than the minimum allowed deposition thickness, t(3|3;5)<$t_{min}$, or (2) adding a $3^{rd}$ sub-sub-layer l(3|3;5) to the instance 606-4 of the ICE would degrade its performance. In view of the foregoing finding, the forming of the $3^{rd}$ sub-layer l(3;5)—and thus of the critical layer L(5)—is completed.

In this example, the next layer L(6) to be formed is a non-critical layer. Hence, the non-critical layer L(6) is deposited, by the fabrication system 300 in accordance with the process 400, to a target thickness t(6) using a single deposition step. At the end of the current iteration (6), an instance 606-5 of the ICE includes the deposited layers L(1), L(2), L(3), L(4), L(5) and L(6). The thickness of the deposited sixth layer L(6) is determined, by the measurement system 304 associated with the fabrication system 300, to be t'(6).

Another example of forming a critical layer of an ICE design using multiple forming steps to form respective sub-layers of the critical layer in accordance with the process 650 is described below.

Example 3

Figure 6C:
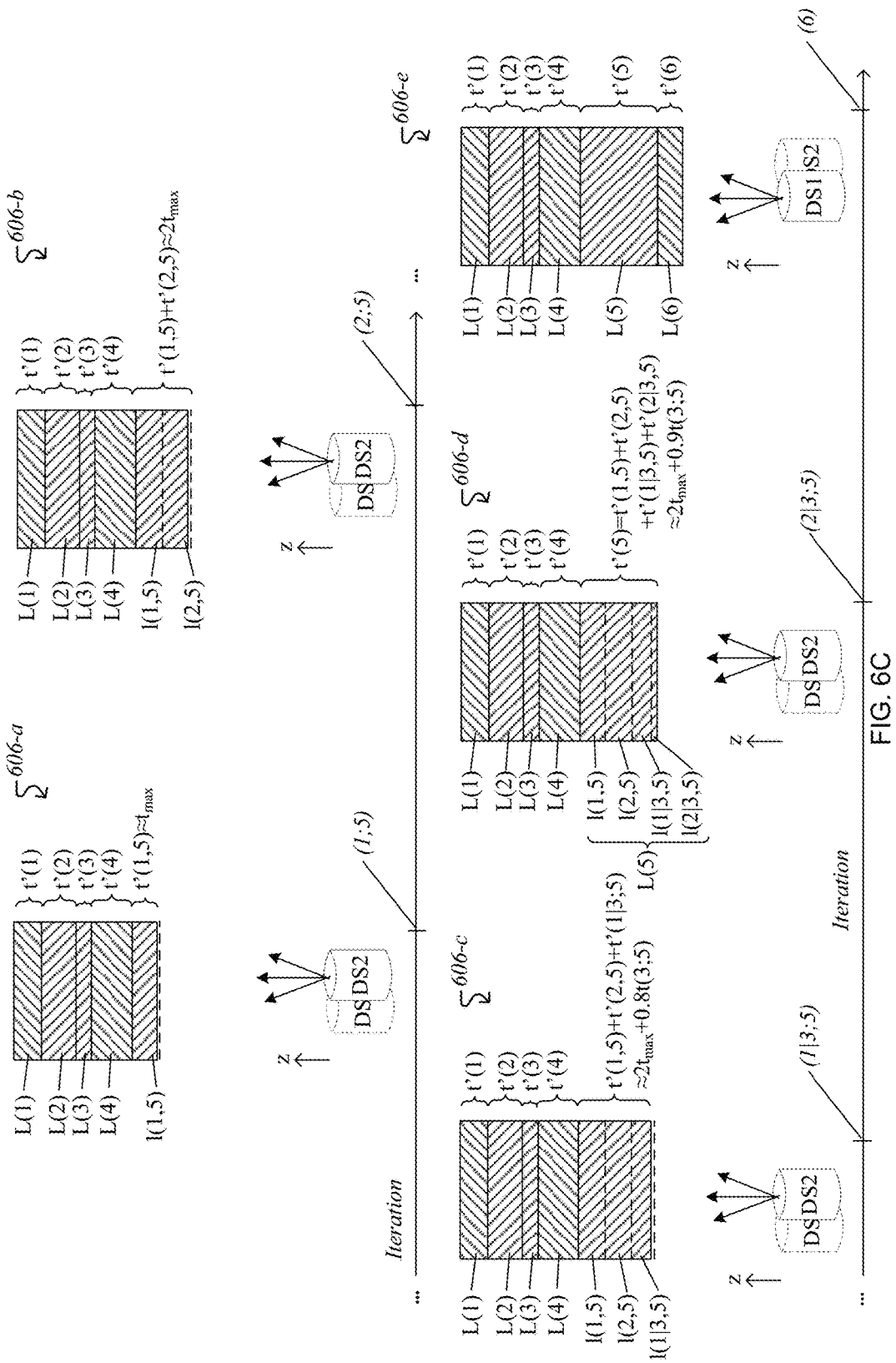

FIG. 6C shows other aspects of forming a critical layer L(5) of the ICE design 245 described above in connection with FIGS. 2A-2B. In this example, another implementation of the process 650 is used to form the critical layer L(5). Prior to forming the critical layer L(5), layers L(1), L(2), L(3) and L(4) were formed in accordance with the process 400, and their thicknesses were determined to be t'(1), t'(2), t'(3) and t'(4), respectively. Additionally, target thicknesses t(5), t(6), t(7) and t(8) of the layers remaining to be formed have been updated based on the determined thicknesses of the formed layers, in accordance with step 440 of the process 400. In this example, the first two sub-layers of the critical layer L(5) will be formed using a predetermined sub-layer target thickness $t(1;5)=t(2;5)=t_{max}$, where $t_{max}$ is a maximum allowed deposition thickness for the fabrication system 300. In this manner, the number Z of sub-layers to be deposited to a predetermined sub-layer target thickness is minimized.

A first iteration (1;5) of the forming of the critical layer L(5) is performed to form the first sub-layer l(1;5) to the predetermined sub-layer target thickness $t(1;5)=t_{max}$. Hence, the first sub-layer l(1;5) is deposited, by the fabrication system 300, to the first sub-layer target thickness t(1;5) using a single deposition step. At the end of the first iteration (1;5), an instance 606-a of the ICE includes the deposited layers L(1), L(2), L(3), L(4) and a first deposited sub-layer l(1;5) of the critical layer L(5). The thickness of the deposited first sub-layer l(1;5) is determined to be t'(1,5) by the measurement system 304 associated with the fabrication system 300.

A second and last iteration (2;5) of the forming of the critical layer L(5) is performed to form the second sub-layer l(2;5) to the predetermined sub-layer target thickness $t(2;5)=t_{max}$ using a single deposition step. At the end of the second iteration (2;5), an instance 606-b of the ICE includes the deposited layers L(1), L(2), L(3), L(4) and first two deposited sub-layers l(1;5), l(2;5) of the critical layer L(5). The thickness of the deposited second sub-layer l(2;5) is determined, by the measurement system 304 associated with the fabrication system 300, to be t'(2,5). Hence, a cumulative thickness of the first two deposited sub-layers l(1;5), l(2;5) of the critical layer L(5) is $t'(1;5)+t'(2;5)\approx 2t_{max}$.

The process 550—described above in connection with FIG. 5A—is used next to form a $3^{rd}$ sub-layer l(3;5) of the critical layer L(5) to a $3^{rd}$ sub-layer target thickness t(3;5). The latter is obtained—in accordance with the Equation (3) based on the target thickness t(5) of the critical layer L(5) and the determined thicknesses t'(1;5), t'(2;5) of the first two deposited sub-layers—to be t(3;5)=t(5)−t'(1;5)−t'(2;5). In this manner, the $3^{rd}$ sub-layer l(3;5) will be formed using two or more forming steps to form respective sub-sub-layers l(n|3;5) thereof, where n=1, 2, . . . .

Prior to a $1^{st}$ iteration (1|3;5) of the forming of the $3^{rd}$ sub-layer l(3;5), a $1^{st}$ target thickness t(1|3;5)=0.8t(3;5) of a $1^{st}$ sub-sub-layer l(1|3;5) is obtained in accordance with Equation (1'), based on the $3^{rd}$ sub-layer target thickness t(3;5) of the $3^{rd}$ sub-layer l(3;5) and a fraction f(1)=0.8. The $1^{st}$ sub-sub-layer l(1|3;5) of the $3^{rd}$ sub-layer l(3;5) is deposited, by the fabrication system 300, to the $1^{st}$ target thickness t(1|3;5) using a single deposition step. At the end of this iteration (1|3;5), an instance 606-c of the ICE includes the deposited layers L(1), L(2), L(3), L(4) and a $1^{st}$ deposited sub-sub-layer l(1|3;5) of the $3^{rd}$ sub-layer l(3;5) of the critical layer L(5). The thickness of the $1^{st}$ deposited sub-sub-layer l(1|3;5) is determined, by the measurement system 304 associated with the fabrication system 300, to be t'(1|3;5). At this time, a $2^{nd}$ target thickness $t(2|3;5)=0.5[t(3;5)-t'(1|3;5)]\approx 0.1t(3;5)$ for the $2^{nd}$ sub-sub-layer l(2|3;5) to be deposited next is obtained in accordance with Equation (1'), based on the target thickness of the $3^{th}$ critical sub-layer t(3;5), the determined thickness t'(1|3;5) of the $1^{st}$ deposited sub-sub-layer l(1|3;5), and a fraction f(2)=0.5. Moreover, here it is verified that (1) the obtained $2^{nd}$ target thickness t(2|3;5) is larger than a minimum allowed deposition thickness, $t(2|3;5)>t_{min}$, and (2) adding a $2^{nd}$ sub-sub-layer l(2|3;5) to the instance 606-c of the ICE would improve its performance.

In view of the foregoing verification, a $2^{nd}$ iteration (2|3;5) of the forming of the $3^{rd}$ sub-layer l(3;5) is performed. The $2^{nd}$ sub-sub-layer l(2|3;5) is deposited, by the fabrication system 300, to the obtained $2^{nd}$ target thickness t(2|3;5) using a single deposition step. At the end of this iteration (2|3;5), an instance 606-d of the ICE includes the deposited layers L(1), L(2), L(3), L(4) and first two deposited sub-sub-layers l(1|3;5), l(2|3;5) of the $3^{rd}$ sub-layer l(3;5) of the critical layer L(5). The thickness of the deposited $2^{nd}$ sub-sub-layer l(2|3;5) is determined, by the measurement system 304 associated with the fabrication system 300, to be t'(2|3,5). Hence, a cumulative thickness of the first two deposited sub-sub-layers layers l(1|3;5), l(2|3;5) of the $3^{th}$ sub-layer l(3;5) of the critical layer L(5) is $t'(1|3;5)+t'(2|3;5)\approx 0.9t(3;5)$. At this time, a $3^{th}$ target thickness $t(3|3;5)=0.5[t(5)-t'(1|3,5)-t'(2|3,5)]\approx 0.05t(3;5)$ for the $3^{rd}$ sub-sub-layer l(3|3;5) to be deposited next is obtained in accordance with Equation (1'), based on the target thickness of the $3^{th}$ critical sub-layer t(3;5), the determined thickness t'(1|3;5), t'(2|3;5) of the first two deposited sub-sub-layers l(1|3;5), l(2|3;5), and a fraction f(3)=0.5. Here, it is found that either (1) the obtained $3^{rd}$ target thickness t(3|3;5) is smaller than the minimum allowed deposition thickness, $t(3|3;5)<t_{min}$, or (2) adding a $3^{rd}$ sub-sub-layer l(3|3;5) to the instance 606-d of the ICE would degrade its performance. In view of the foregoing finding, the forming of the $3^{rd}$ sub-layer l(3;5)—and thus of the critical layer L(5)—is completed.

In this example, the next layer L(6) to be formed is a non-critical layer. Hence, the non-critical layer L(6) is deposited, by the fabrication system 300 in accordance with the process 400, to a target thickness t(6) using a single deposition step. At the end of the current iteration (6), an instance 606-e of the ICE includes the deposited layers L(1), L(2), L(3), L(4), L(5) and L(6). The thickness of the deposited sixth layer L(6) is determined, by the measurement system 304 associated with the fabrication system 300, to be t'(6).

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. A method performed by a fabrication system, the method comprising:
   receiving a design of an integrated computational element (ICE), the ICE design comprising
      specification of a substrate and a plurality of layers, their respective target thicknesses and complex refractive indices, wherein complex refractive indices of adjacent layers are different from each other, and wherein fabrication of an ICE in accordance with the ICE design is related to a characteristic of a sample, and
      identification of one or more critical layers from among the plurality of layers, wherein a layer of the ICE is identified as a critical layer if potential variations of the layer's thickness or complex refractive index, due to expected variations of the fabrication, cause degradation of the ICE's performance that exceeds a threshold degradation, otherwise the layer of the ICE is identified as a non-critical layer; and
   forming the layers of the ICE, wherein at least one critical layer of the ICE is formed using two or more forming steps to form respective two or more sub-layers of the critical layer, and at least one non-critical layer of the ICE is formed using a single forming step.

2. The method of claim 1, further comprising
   after said forming of at least one sub-layer or layer, measuring, by a measurement system, characteristics of the formed sub-layers and layers; and
   prior to said forming of at least some of the at least one critical layer of the ICE, adjusting said forming of layers remaining to be formed based on results of said measuring.

3. The method of claim 2, further comprising, prior to said forming of at least some of the two or more sub-layers of at least one critical layer of the ICE, adjusting said forming of sub-layers remaining to be formed for the critical layer based on the results of said measuring.

4. The method of claim 2, wherein the results of said measuring comprise one or more of complex refractive indices and thicknesses of the formed sub-layers and layers.

5. The method of claim 4, wherein said measuring comprises performing ellipsometry of the formed sub-layers and layers.

6. The method of claim 4, wherein said measuring comprises performing optical monitoring of the formed sub-layers and layers.

7. The method of claim 4, wherein said measuring comprises performing spectroscopy of the formed sub-layers and layers.

8. The method of claim 4, wherein said measuring comprises performing physical monitoring of the formed sub-layers and layers.

9. The method of claim 4, wherein said adjusting comprises obtaining target thicknesses of the remaining sub-layers of the critical layer currently being formed and the layers remaining to be formed based on the complex refractive indices and thicknesses of the formed sub-layers and layers.

10. The method of claim 4, wherein said adjusting comprises updating a deposition rate or time used to form remaining sub-layers of the critical layer currently being formed and the layers remaining to be formed based on the complex refractive indices and thicknesses of the formed sub-layers and layers.

11. The method of claim 4, wherein said adjusting comprises modifying a complex refractive index of remaining sub-layers of the critical layer currently being formed and complex refractive indices corresponding to the layers remaining to be formed based on the complex refractive indices and thicknesses of the formed sub-layers and layers.

12. The method of claim 1, wherein said forming of the layers of the ICE comprises
    forming each critical layer of the ICE using two or more forming steps to form respective two or more sub-layers of the critical layer, and
    forming each non-critical layer of the ICE using a single forming step.

13. The method of claim 12, further comprising
    after said forming of each sub-layer or layer, measuring, by a measurement system, characteristics of the formed sub-layers and layers; and
    prior to said forming of at least some of the one or more critical layers of the ICE, adjusting said forming of layers remaining to be formed based on results of said measuring.

14. The method of claim 1, further comprising, for at least one critical layer, forming at least some sub-layers of the two or more sub-layers to a sub-layer target thickness equal to a fraction of the remaining thickness of the critical layer.

15. The method of claim 14, wherein the fraction of the remaining thickness of the critical layer is 40-60%.

16. The method of claim 14, wherein the fraction of the remaining thickness of the critical layer is 85-95%.

17. The method of claim 14, wherein
    a first fraction is used for the sub-layer target thickness of a first sub-layer of the two or more sub-layers, and
    a second fraction is used for sub-layer target thickness of the remaining ones of the two or more sub-layers.

18. The method of claim 1, further comprising, for at least one critical layer,
    determining, by the fabrication system after completing a current number of sub-layers of the critical layer, that forming another sub-layer in addition to the current number of sub-layers would lead to degradation in performance of the ICE with the current number of sub-layers in the critical layer; and
    completing of said forming the critical layer in response to said determining.

19. The method of claim 1, further comprising, for at least one critical layer, forming at least some of the two or more sub-layers to a sub-layer target thickness equal to a fraction of the target thickness of the critical layer.

20. The method of claim 19, wherein the fraction of the target thickness is configured such that the sub-layer target thickness is no less than a minimum allowed sub-layer thickness and does not exceed a maximum allowed sub-layer thickness.

21. The method of claim 20, wherein the fraction of the target thickness further is configured to form a minimum number of sub-layers, based on the maximum allowed sub-layer thickness.

22. The method of claim 20, wherein the minimum and maximum allowed sub-layer thicknesses are constrained by limitations of a deposition process used to form the sub-layers.

23. The method of claim 20, wherein the minimum and maximum allowed sub-layer thicknesses are constrained by limitations of a monitoring technique used to monitor thickness of the formed sub-layers.

* * * * *